US006048717A

United States Patent [19]
Paul et al.

[11] Patent Number: 6,048,717

[45] Date of Patent: *Apr. 11, 2000

[54] INHIBITORS OF CATALYTIC ANTIBODIES

[75] Inventors: Sudhir Paul, Omaha, Nebr.; Michael J. Powell, Gaithersberg; Richard J. Massey, Rockville, both of Md.

[73] Assignee: IGEN International, Inc., Gaithersburg, Md.

[*] Notice: This patent is subject to a terminal disclaimer.

[21] Appl. No.: 08/478,285

[22] Filed: Jun. 7, 1995

Related U.S. Application Data

[60] Continuation of application No. 08/009,915, Jan. 27, 1993, abandoned, which is a division of application No. 07/486,594, Feb. 28, 1990, Pat. No. 5,194,585, which is a continuation-in-part of application No. 07/343,081, Apr. 25, 1989, Pat. No. 5,236,836.

[51] Int. Cl.$^7$ ........................................... C12N 9/00
[52] U.S. Cl. ......................... 435/188.5; 514/14; 530/327
[58] Field of Search ..................... 435/188.5; 530/327, 530/328, 329; 514/14

[56] References Cited

U.S. PATENT DOCUMENTS

| | | | |
|---|---|---|---|
| 4,196,265 | 4/1980 | Koprowski et al. | 435/172.3 |
| 4,376,110 | 3/1983 | David et al. | 436/513 |
| 4,492,751 | 1/1985 | Boguslaski et al. | 435/7.92 |
| 4,493,890 | 1/1985 | Morris | 435/7.92 |
| 4,659,567 | 4/1987 | Tramontano et al. | 530/387 |
| 4,661,586 | 4/1987 | Levy et al. | 530/387.2 |
| 4,792,446 | 12/1988 | Kim et al. | 424/85.8 |
| 4,888,281 | 12/1989 | Schochetman | 435/72 |
| 4,900,674 | 2/1990 | Benkovic | 435/237 |
| 5,079,152 | 1/1992 | Benkovic et al. | 435/125 |
| 5,236,825 | 8/1993 | Iverson et al. | 435/68.1 |

FOREIGN PATENT DOCUMENTS

| | | |
|---|---|---|
| 0125023 | 11/1984 | European Pat. Off. . |
| 0251093 | 1/1988 | European Pat. Off. . |
| 0260939 | 3/1988 | European Pat. Off. . |
| WO 85/02414 | 6/1985 | WIPO . |
| WO 86/06742 | 11/1986 | WIPO . |
| PCT/US89/01950 | 11/1989 | WIPO . |
| WO 89/10754 | 11/1989 | WIPO . |
| WO 90/05746 | 5/1990 | WIPO . |
| Wo 90/05144 | 5/1990 | WIPO . |

OTHER PUBLICATIONS

Pauling, L., *Nature 161*, 707, (1948).

Kohen, F., Kim, J.B., Lindner, H.R., Eshhar, Z., Green, B., "Antibody enhanced hydrolysis of steroid esters", *Bioch. et Bioph. Acta 629*, 328–337 (1980).

Pollack, S.J., Jacobs, J.W., Schultz, P.G., *Science 234*, 1570 (1986).

A. Tramontano, A.A. Amman, R.A. Lerner, *J. Am. Chem. Soc. 110*, 2282 (1988).

K.D. Janda, D. Schloeder, S.J. Benkovic, R.A. Lerner, *Science 241*: 1188 (1988).

C.N. Durfor, R.J. Bolin, R.J. Sugasawara, R.J. Massey, J.W. Jacobs, P.G. Schultz, *J. Am. Chem. Soc.* 110:8713 (1988).

Jackson, D.Y. et al., *J. Am. Chem. Soc. 110*, 4841 (1988).

D. Hilvert, S.H. Carpenter, K.D. Nared, N.T. Auditor, *Proc. Natl. Acad. Sci. USA* 85: 4953 (1988).

Shokat, K. Leumann, C.H. Sugasawara, R.J., Schultz, P.G., *Angew. Chem. Int. Ed. Engl. 27*, 1172 (1988).

Paul, S. et al., Catalytic hydrolysis of vasoactive intestinal peptide by human autoantibody. *Science* 244:1158–1161 (1989).

Paul, S., Erian, P.H., Said, S.I., "Autoantibody to vasoactive intestinal peptide in human circulation", *Biochem. Biophys. Res. Commun. 130*, 479–485, 1985.

Paul, S., Said, S.I., "Human autoantibody to vasoactive intestinal peptide: Increased incidence in muscular exercise", *Life Sciences 43*, 1079–1084, 1988.

Paul, S., Said, S.I., Thompson, A., Volle, D.J., Agrawal, D.K., Foda, H., De la Rocha, S. "Characterization of autoantibodies to VIP in asthma", *J.Neuroimmunol. 23*, 133–142 (1989).

Itoh, N., Obata, K.–I., Yanaihara N., Okamoto, H., "Human preprovasoactive intestinal polypeptide contains a novel PHI–27–like peptide, PHM–27", *Nature 304*, 547–549, (1983).

Bloom, S.R., Barnes, A. J. Adrian, T.E., Polak, J.M., "Autoimmunity in diabetics induced by hormonal contaminants of insulin", *Lancet*, 14–17, (1979).

Ruff, M.R., Martin, B.M., Ginns, E.I., Farrar, W.L., Pert, C.B. CD4 receptor binding peptides that block HIV infectivity cause human monocyte chemotaxis. *FEBS Lett.* 211:17–22 (1987).

Nilsson, A., Structure of the vasoactive intestinal peptide from chicken intestine. The amino acid sequence. *FEBS Lett.* 60:322–326 (1975).

Dimaline, R., Thorndyke, M.C., Purification and characterization of VIP from two species of dogfish. *Peptides* 7(Suppl.1):21–26 (1986).

Paul, S., Chou, J., Beckham, S., Liu, L.–W, Kubota, E., Dominguez, N., Said, S.I., Elevated levels of atrial natriuretic peptide and vasoactive intestinal peptide in exercising man. *Clin. Res.* (abstr.) 35:112A (1987).

Rosselin, G., The receptors for the VIP family peptides (VIP, secretin, GRF, PHI, PHM, GIP, glucagon and oxyntomodulin). Specificites and identity. *Peptides* 7(Suppl. 1):89–100 (1986).

(List continued on next page.)

*Primary Examiner*—Charles L. Patterson, Jr.
*Attorney, Agent, or Firm*—Whitman Breed Abbott & Morgan LLP

[57] ABSTRACT

Specific, selective inhibitors of catalytic antibodies both synthetic and naturally occurring, their use and compositions thereof are disclosed. In particular, an inhibitor preventing the hydrolysis of the peptide bond between amino acid residues 16 and 17 in the neurotransmitter vasoactive intestinal peptide (VIP) by an anti-VIP catalytic autoantibody is disclosed.

14 Claims, 18 Drawing Sheets

OTHER PUBLICATIONS

Paul, S., Said, S.I., "Characterization of receptors for vasoactive intestinal peptide from the lung", *J. Biol. Chem.* 262, 158–162 (1987).

Barret, A.J. and Salvesen, A., eds., *Proteinase Inhibitors,* Elsevier, London 3–22 (1986).

Meek, L.D. et al., "Inhibition of HIV–1 Protease In Infected T–Lymphocytes By Synthetic Analogues", *Nature* 343: 390–392 (1990).

Amit, A.G., Mariuzza, R.A., Philips, S.E.V., Poljak, R.J., *Science* 233: 747 (1986).

S. Sheriff, et al., *Proc. Natl. Acad. Sci. (USA)* 84: 8075 (1987).

van Regenmortel, R.H.V., *Synthetic Peptides as Antigens,* Laboratory Techniques in Biochemistry and Molecular Biology Series, (Eds: R.H. Burdon and P.H. van Knippenberg, 19: 1–39 (1988).

Rich, D.H., *Proteinase Inhibitors,* (Eds. A.J. Barrett and G. Salvesen, Elsevier), 179–217 (1986).

Paul, S., Wood, K., Said, S.I., "Purification of [$^{125}$I]–Vasoactive intestinal peptide by reverse–phase HPLC", *Peptides* 5, 1085–1087 (1984).

Turner, J.T., Bylund, D.B., "Characterization of the VIP receptor in rat submandibular bland: Radioligand binding assay in membrane preparations", *J. Pharmacol Exp. Therap.* 242, 873–881 (1987).

*Affinity Chromatography Principles and Methods,* Pharmacia, Uppsala, Sweden, 12–18 (1986).

Stewart, J.M. and Young, J.D., *Solid Phase Peptide Synthesis,* Pierce Chemical Co., Rockford, Illinois (1984).

FPLC™ Ion Exchange and Chromatofocusing, Pharmacia, Uppsala, Sweden, 1–171 (1985).

*PhastGel Silver Kit Instruction Manual.* Pharmacia (Uppsala, Sweden 1987).

Baldwin, E. and Schultz, P.G., Generation of a catalytic antibody by site–directed mutagenesis. *Science,* 244:1152 (1989).

Dixon, M., Webb, E.C. et al., *Enzymes,* 3d Ed. Longman, (London 1979).

Schultz, P.G., Catalytic antibodies. *Acc. Chem. Res.* 22:287 (1989).

Blackburn, G.M., Kang, A.S. et Catalytic antibodies. *Biochem. J.* 262:381 (1989).

Steinitz, M., Klein, G., Koskimies, S., Makela, O., "EB Virus induced B lymphocyte lines producing specific antibodies", *Nature* 269, 420–422 (1977).

Tramontano, A. et al., "Chemical Reactivity At An Antibody Binding Site Elicited By Mechanistic Design Of A Synthetic Antigen", *P.N.A.S.(USA),* 83, 6736–6740 (1986).

Pollack, S.J., and Schultz, P.G., "Antibody Catalysis by Transition State Stabilization", *Cold Spring Harbor Symposium on Quantitative Biology,* 52, 97–104 (1987).

Tramontano, A. et al., "Catalytic Antibodies", *Science,* 234, 1566–1570 (1986).

Lerner, R.A. and Tramontano, A., "Antibodies as Enzymes", *Trends. Biochem. Science,* 12(II), 427–430 (1987).

Cochran, A.G. et al., "Photosensitized Cleavage of a Thymine Dimer by an Antibody", *J.Am. Chem. Soc. 110:* 7888–7890 (1988).

Lerner, R.A. and Tramontano, A., "Catalytic Antibodies", *Scientific American,* 258(3), 42–50 (1988).

Iverson, B.L. and Lerner, R.A., "Sequence–specific peptide cleavage catalyzed by an antibody", *Science,* 243, 1184–1188 (1989).

Baum, R., "Catalytic Antibody Cuts Peptide Bond", *C&EN* 5, 7–8 (1989).

Schultz, P.G., "The Interplay Between Chemistry and Biology in the Design of Enzymatic Catalysts" *Science 240,* 426 (1988).

Van Brunt, J., "Antibodies Find a New Role—As Enzymes", *Biotechnology,* 5, 767 (1987).

Moe, K., "Scripps, UC Create 'Killer' Antibodies", *S.D. Union,* Dec. 12, 1986.

"Making Antibodies Act Like Enzymes", *Science News,* 130, Nos. 25 & 26, Dec. 20 & 27, 1986.

Bulletin, Office of Public Information, Berkeley Campus, University of California, Dec. 9, 1986.

Marx, J. "Making Antibodies Work Like Enzymes", *Science,* 234, 1497–1498 (1986).

Jacobs, J. et al., "Catalytic Antibodies", *J. Am. Chem. Soc.,* 109, 2174–2176 (1987).

"Antibody Catalyzes Stereospecific Reaction", Science/Technology Concentrates, *C&EN,* 15, Aug. 31, 1987.

Baum, R.M., "Catalytic Antibodies Open Up New Strategy For Protein Engineering", *Science, C&EN,* 30–33, Apr. 6, 1987.

Napper, A., "A Stereospecific Cyclization Catalyzed By An Antibody", *Science,* 237, 1041–1043 (1987).

Hansen, D., "Antibodies With Some Bite", *Nature,* 325, 304 (1987).

"Abzylutely Spot On", *The Economist,* 80–81, Feb. 7, 1987.

"Cancer Breakthrough Seen—IGEN Discovers New Protein Class", *Rockville Gazette,* Jan. 21, 1987.

Massey, R., "Catalytic Antibodies Catching On", Reprint from *Nature,* 328, No. 6129, 457–458 (1987).

Highfeld, R., "Aids Drug A Step Nearer", *The Daily Telegraph,* 9, Aug. 4, 1987.

"Abzymes", *Scientific American,* 256, No. 2, 84–85 (1987).

Steinitz, M., Seppala, I., Eichmann, K., Klein, G., "Establishment of a Human Lymphoblastoid Cell Line with Specific antibody production against group A streptococcal carbohydrate", *Immunobiology 156,* 41–47 (1979).

Steinitz, M., Izak, G., Cohen, S., Ehrenfeld, M., Flechner, I., "Continuous production of monoclonal rheumatoid Factor by EBV–transformed lymphocytes", *Nature 287,* 443–445, (1980).

Kozbor, D., Steinitz, M. Klein, G., Koskimies, S., Maketa, O., "Establishment of anti–TNP antibody–producing human lymphoid lines by preselection for hapten binding followed by EBV transformation", *Scand. J. Immunol. 10,* 187–194 (1979).

Kozbor, D. & Roder, J., The production of monoclonal antibodies from human lymphocytes. *Immunology Today 4,* 72–79 (1983).

Roder, J., Cole, D., Kozbor, D., "The EBV–Hybridoma Technique", *Methods in Enzymology 121,* 140–167 (1986).

Kohler G., Milstein C., "Continuous Cultures of Fused Cells Secreting Antibody of Predefined Specificity", *Nature 256,* 445–497 (1975).

W. P. Jencks, "Catalysis In Chemistry And Enzymology", 288 (McGraw Hill, New York 1969).

Slobin, L., "Preparation And Some Properties Of Antibodies With Specificity Towards p–Nitrophenylesters", *Biochemistry,* 5, 2836–2844 (1966).

Raso, V. and Stollar, B.D., "The Antibody–Enzyme Analogy. Characterization Of Antibodies To Phosphopyrido–xyltyrosine Derivatives", *Biochemistry,* 14, 584–591 (1975).

Raso, V., and Stollar, B.D., "Antibodies Specific For Conformationally Distinct Coenzyme Substrate Transition State Analogs . . . ", *J. Am. Chem. Soc.*, 95(5), 1621–1628 (1973).

Raso, V., and Stollar, B.D., "The Antibody–Enzyme Analogy. Comparison Of Enzymes And Antibodies Specific For Phosphopyriodoxyltyrosine", *Biochemistry*, 14, 591–599 (1975).

Burd, J. et al., "Specific Protein–Binding Reactions Monitored By Enzymatic Hydrolysis Of Ligands–Fluorescent Dye Conjugates", *Analytical Biochemistry*, 77, 56–67 (1977).

Kohen, F. et al., "A Steroid Immunoassay Based On Antibody–Enhanced Hydrolysis Of A Steroid–Umbelliferone Conjugate", *FEBS Letters*, 100, 137–140 (1979).

Kohen, F. et al., "Nonradioisotopic Homogeneous Steroid Immunoassays", *J. Steroid Biochemistry*, 11, 161–167 (1979).

Kohen, F. et al., "Monoclonal Immunoglobulin G Augments Hydrolysis Of An Ester Of The Homologous Hapten", *FEBS Letters*, 111, 427–431 (1980).

Kohen et al., *FEBS Letters*, 104, 201–205 (1979).

Royer, G.P., "Enzyme–Like Synthetic Catalysts (Synzymes)", *Advances In Catalysis*, 29, 197–227 (1980).

Summers, J.B., Jr., "Catalytic Principles Of Enzyme Chemistry: Antibody Models And Stereo Electronic Control", Harvard University Ph.D. Thesis, 22–101 (1983).

Lerner, R.A., "Antibodies Of Predetermined Specificity In Biology And Medicine", *Adv. In Immun.*, 36, 1–40 (1984).

Frackelton, A.R., Jr. et al., "Functional Diversity Of Antibodies Elicited By Bacterial β–D Galactosidase", *J. Bio. Chem.*, 255 (11), 5286–5290 (1980).

White A. et al., *Principles of Biochemistry*, 200, 201, 217–221, 573, 575 and 585 (McGraw Hill Book Company, New York Fourth ed. 1968).

Roberts, R.J., "Directory Of Restriction Endonuclease", *Methods In Enzymology*, 68, 27–31 (Academic Press, New York, R. Wu, Editor (1979).

David G.S., et al., "The Hybridoma—An Immunochemical Laser", *Clin. Chem.*, 27 (9), 1580–1585 (1981).

Sacks, D.L. et al., "Immunization Of Mice Against African Trypanosomiasis Using Anti–Idiotypic Antibodies", *J. Expr. Med.*, 155, 1108–1119 (1982).

Jencks, W.P., *Adv. Enzym.*, 43, 219–410 (1975).

Jencks, W.P., *Molecular Biol. Biochem. & Biophys.*, 32, 3–25 (1980).

Milstein, C., *Sci. Am.*, 234(4), 66–74 (1980).

Kwan, S. et al., "Production of Monoclonal Antibodies", *Genetic Engineering*, 2, 31–46 (1980).

Melchers, F. et al., "Enhanced Stability Against Heat Denaturization Of *E. Coli* Wild Type And Mutant β–Galactosidase In The Presence Of Specific Antibodies", *Biochemical And Biophysical Research Communications*, 40(3), 570–575 (1970).

Altschuh, D. et al., "Localization of Antigenic Determinants of a Viral Protein by Inhibition of Enzyme–Linked Immunosorbent Assay (ELISA) with Tryptic Peptides", *J. Immunology Methods*, v. 50, p. 99 (1982).

Amzel, L.M. et al., "Three–Dimensional Structure of Immunoglobulins", *Ann. Rev. Biochem.* 48:961 (1979).

Anglister, J. et al., "NMR study of the Complexes Between a Synthetic Peptide Derived from the B subunit of Cholera Toxin and Three Monoclonal Antibodies Against It", *Abstract, American Chemical Soc.* (1988), 006–2960/88/0427–0717.

Aruffo, A. et al., "Molecular Cloning of a CD38 cDNA by a high–efficiency COS cell expression system", *Proc. Natl. Acad. Sci.*, 84: 8573–8577 (1987).

Atassi, M. Z., "Surface–Simulation Synthesis and Its Application in Protein Molecular Recognition", *Protein Engineering—Applications in Science, Medicine and Industry*, pp. 125–153 Edited by Inouye, M. and Sarma, R., Academic Press (1986).

Azuma, T. et al., "Diversity of the Variable–Joining Region Boundary of λ Light Chains has a Pronounced Effect on Immunoglobulin Ligand–Binding Activity", *Proc. Natl. Acad. Sci. USA*, v. 81, p. 6139 (Oct. 1984).

Baldwin, E. et al., "Generation of a catalytic antibody by site–directed mutagenesis", *Science* v.245, pp. 1104–1107 (1989).

Barrett, A. J., *Proteinase Inhibitors* (Editors A. J. Barrett and G. Salvesen), pp. 3–22, Elsevier, London, (1986).

Benjamini, E. et al., "Immunochemical Studies on the Tobacco Mosaic Virus Protein. VI. Characterization of Antibody Population Following Immunization with TMV Protein", *Biochemistry*, v.7, No. 4, pp. 1253–1260 (1968).

Benjamini, E. et al., "Immunochemical Studies on the Tobacco Mosaic Virus Protein. VII. The Binding of Octanoylated Peptides of the TMV Protein with Antibodies to the Whole Protein", *Biochemistry*, v.7, No. 4, pp. 1261–1264 (1968).

Better, M. et al., "*Escherichia Coli* Secretion of an Active Chimeric Antibody Fragment", *Science*, 240: 1041–1043 (1988).

Chalufour, A. et al., "Rare Sequence Motifs are Common Constituents of Hypervariable Antibody Regions", *Ann. Inst. Pasteur/Immunology*, 138:671, Elsevier, Paris (1987).

Chaudhary, V. J. et al., "A recombinant immunotoxin consisting of two antibody variable domains fused to Pseudomonas exotoxin", *Nature* 339:394 (1989).

Chothia, C. et al., "Canonical Structures for the Hypervariable Regions of Immunoglobulins", *J. Mol. Biol. 196:*901 (1987).

Chothia, C. et al., "The Predicted Structure of Immunoglobulin D1.3 and Its Comparison with the Crystal Structure", *Reports*, 755 (Aug. 1986).

Colman, P. M. et al., "Three–Dimensional Structure of a Complex of Antibody with Influenza Virus Neuraminidase", *Nature 326*: 358 (Mar. 1987).

Corey, D.R. et al., "Generation of a Hybrid Sequence–Specific Single–Stranded Deoxyribonuclease", *Reports* 1401 (Dec. 1987).

de la Paz, P. et al., "Modelling of the Combining Sites of Three Anti–Lysozyme Monoclonal Antibodies and of the Complex Between One of the Antibodies and its Epitope", *EMBO J.*, 5:2, 415 (1986).

Dimaline R. et al., "A novel VIP from elasmobranch intestine has full affinity for mammalian pancreatic VIP receptors", *Biochimica et Biophysica Acta*, 930, 97–100 (1987).

Dimaline, R. et al., "Purification and Characterization of VIP from Two Species of Dogfish", *Peptides*, 7(Suppl. 1): 21–26 (1986).

Dixon, M. et al., *Enzymes*, Third Edition, London, (1979).

Edelman, G. M. et al., "Reconstruction of Immunologic Activity by Interaction of Polypeptide Chains of Antibodies", *Proc. Natl. Acad. Sci.*, 50: 753–761 (1963).

Emr, S. D. et al., "Sequence analysis of mutations that prevent export of λ receptor, an *Escherichia coli* outer membrane protein", *Nature*, 285: 82–85 (1980).

Erhan, S. et al., "Do immunoglobulins have proteolytic activity?", *Nature,* v.251, pp. 353–355 (Sep. 27, 1974).

Fisher, G., "Acyl Group Transfer–Aspartic Proteinases", *Enzyme Mechanisms* (Editors: M. I. Page and A. Williams), Royal Society of Chemistry, London, 230 (1987).

*FPLC™ Ion Exchange and Chromatofocusing—Principles and Methods,* Pharmacia, pp. 59–106, Uppsala, Sweden (1987).

Franek, F. and Nezlin, R. S., "Recovery of Antibody Combining Activity By Interaction of Different Peptide Chains Isolated from Purified Horse Antitoxins", *Folia Microbiol.,* 8: 128–130 (1963).

Franek, F. and Nezlin, R. S., *Biokhimiya,* 28: 193 (1963).

Gavish, M. et al., "Preparation of a Semisynthetic Antibody", Abstract, *Am. Chem. Soc.* (1978), 006–2960/78/0417–1345.

Geysen, H. M. et al., "A Priori Delineation of a Peptide Which Mimics a Discontinuous Antigenic Determinant", *Molecular Immunology,* 23:7 p. 709 (1986).

Giam, C. Z. et al., "In Vivo and In Vitro Autoprocessing of Human Immunodeficiency Virus Protease Expressed in *Escherichia Coli*", *J. Biol. Chem.,* 263: 14617–14620 (1985).

Gish et al., *J. Med. Chem.,* 14: 1159–1162, (1971).

Harper, J. W. et al., "Enzymatically Active Angiogenin/Ribonuclease A Hybrids Formed by Peptide Interchange", Abstract,*Am. Chem. Soc.* (1988), 006–2960/88/0427–0219.

Hendershot, L. M. et al., "Identity of the Immunoglobulin Heavy–Chain–Binding Protein with the 78,000–Dalton Glucose–Regulated Protein and the Role of Posttranslational Modifications in Its Binding Function", *Mol. and Cellular Bio.,* 8(10), 4250–4256, (1988).

Hochman, J. et al., "An Activity Antibody Fragment (Fv) Composed of the Variable Portions of Heavy and Light Chains", *Biochemistry 12:* 1130 (1973).

Huse, W. D. et al., "Generation of a Large Combinatorial Library of the Immunoglobulin Repertoire in Phage Lambda", *Science,* 246: 1275–1281 (1989).

Inbar, D. et al., "Localization of Antibody–Combining Sites within the Variable Portions of Heavy and Light Chains", *Proc. Natl. Acad. Sci. USA,* 69: 2659 (1972).

Inbar, D. et al., "Crystallization with Hapten of the Fab Fragment from a Mouse IgA Myeloma Protein with Antidinitrophenyl Activity",*J. of Biol. Chem. 246:* 6272 (1971).

Iverson, B. L. et al., "Sequence–Specific Peptide Cleavage Catalyzed by an Antibody", *Science 243:*1184 (1989).

Jackson, D. Y. et al., "A Mutagenesis Study of a Catalytic Antibody", *Proc. Natl. Acad. Sci. U.S.A.,* v.88, pp. 58–62, (Jan. 1991).

Jaton, J. C. et al., "Recovery of Antibody Activity upon Reoxidation of Completely Reduced Polyalanyl Heavy Chains and Its Fd Fragment Derived from Anti–2,4–dinitrophenyl Antibody", *Biochemistry,* 7: 4185–4195 (1968).

Jerne et al., "Recurrent Idiotopes and Internal Images," *EMBO Journal* 1:243–247 (1982).

Kabat, E. A. et al., "Sequences of Proteins of Immunological Interest (5th Edition)", v.1, 2, 3, U.S. Department of Health and Human Services (1991).

Klein, J. "Immunology: The Science of Self–Nonself Discrimination", pp. 168–169 (John Wiley & Sons, New York) (1982).

Knisley, K. A. et al., "Affinity Immunoblotting. High Resolution Isoelectric Focusing Analysis of Antibody Clonotype Distribution", *J. Immunological Methods,* 95, 79–87, Elsevier (1986).

Koerner and Nieman, "High Performance Liquid Chromatographic Determination of Glucosides", *J. Chromatography 449,* 216–228, (1988).

Kubiak, T. et al., "Synthetic Peptides $V_H$(27–68) and $V_H$ (16–68) of the Myeloma Immunoglobulin M603 Heavy Chain and their Association with the Natural Light Chain to Form an Antigen Binding Site", Abstract, *Am. Chem. Soc.* (1987), 006–2960/87/0426–7849.

Lee, F. et al., "Isolation and Characterization of a mouse interleukin cDNA clone that expresses B–cell stimulatory factor 1 activities and T–cell and mast–cell stimulating activities", *Proc. Natl. Acad. Sci. U.S.A. 83:* 2061–2065 (1986).

Lerner, R. A. et al., "Catalytic Antibodies", *Scientific American,* 258(3), 42–50 (1988).

Lerner, R. A. et al., "Antibodies as Enzymes", *Trends Biochem. Science,* 12(11), 427–430 (1987).

Lerner et al., *Science,* 252, 659–667 (1991).

Loh, E. Y. et al., "Polymerase Chain Reaction with Single–Sided Specificity: Analysis of T Cell Receptor δ Chain", *Science,* 243: 217–220 (1989).

Lorberboum–Galski, H. et al., "Cytotoxic Activity of an Interleukin 2–Pseudomonas Exotoxin Chimeric Protein Produced in *Escherichia coli*", *Proc. Natl. Acad. Sci. U.S.A.,* 85: 1922–1926 (1988).

MacDonald, R. J. et al., "Isolation of RNA Using Guanidinium Salts", *Meth. Enzymol.,* 152: 219–226 (1987).

Machleidt, W. et al., "Mechanism of Inhibition of Papain by Chicken Egg White Cystatin", (Biomedical Division, Elsevier Science Publishers), v.243, No. 2, p. 234, (Jan. 1989) 00145793/89.

Mariuzza, R. A. et al., "The Structure Basis of Antigen–Antibody Recognition", *Ann. Rev. Biophys. Chem.,* 16: 139 (1987).

Meek, T. D. et al., "Inhibition of HIV–1 Protease in Infected T–Lymphocytes by Synthetic Analogues", *Nature,* 343: 390–392 (1990).

Mierendorf, R. C. et al., "Direct Sequencing of Denatured Plasmid DNA", *Meth. Enzymol.,* 152: 556–562 (1987).

Mutter, M., "The Construction of New Proteins and Enzymes—A Prospect for the Future?", *Agnew. Chem. Int. Ed. Engl.* 24, p. 639 (1985).

Nilsson, A., "Structure of the Vasoactive Intestinal Peptide from Chicken Intestine. The Amino Acid Sequence", *FEBS Letters,* 60: 322–326 (1975).

Nishi, N. et al., "Apparent Autolysis of the N–Terminal Tetrapeptide of VIP", *Chem. Pharm. Bull.* 31(3), p. 1067 (1983).

Offord, R. E., "Review Protein Engineering by Chemical Means?", *Protein Engineering,* v.1, No. 5, p. 151 (1987).

Opstad, K., "The Plasma VIP Response to Exercise is Increased After Prolonged Strain, Sleep and Energy Deficiency and Extinguished by Glucose Infusion", *Peptides,* 8, 175–178 (1986).

Orlandi, R. et al., "Cloning Immunoglobulin variable domains for expression by the polymerase chain reaction", *Proc. Natl. Acad. Sci. U.S.A.,* 86: 3833–3837 (1989).

Paul, S. et al., "High Affinity Peptide Histidine Isoleucine–Preferring Receptors in Rat Liver", *Life Sciences,* v.41, pp. 2373–2380 (1987).

Paul, S. et al., "Regulatory Aspects of the VIP Receptor in Lung", *Annals of New York Academy of Science,* v.527, pp. 282–295 (Jun. 1988).

Paul, S. et al., "Elevated Levels of Atrial Natriuretic Peptide and Vasoactive Intestinal Peptide in Exercising Man", Abstract, *Clin. Res.,* 35: 112A (1987).

Paul, S., "A New Effector Mechanism for Antibodies: Catalytic Cleavage of Peptide Bonds", *Cold Spring Harbor Symposium on Immunological Research,* v.54 (1989).

Paul, S. et al., "Autoabzyme Catalyzed Cleavage of Vasoactive Intestinal Peptide", *Progress in Immunology,* v.VIII, pp. 833–836 (editors F. Melchers et al.) Springer Verlag, Berlin (1989).

*PhastGel Silver Kit Instruction Manual,* Pharmacia, Uppsala, Sweden (1987).

Porter, R. R. et al., "Subunits of Immunoglobulins and their relationship to Antibody Specificity", *J. Cell Physiol.,* 67 (Suppl. 1): 51–64 (1966).

*Proceedings of the Symposium of Immunological Recognition,* vol. III, Springer Verlag (1989).

Rees, A. R. et al., "Investigating Antibody Specificity Using Computer Graphics And Protein Engineering", *Trends in Biochemical Sciences,* 11: 144 (Mar. 1986).

Rich, D. H., "Inhibitors of Aspartic Proteinases", *Proteinase Inhibitors* (Editors A. J. Barrett and G. Salvesen), Elsevier, pp. 179–217 (1986).

Roberts, S. et al., "The Cloning and Expression of an Anti–Peptide Antibody: A System for Rapid Analysis of the Binding Properties of Engineered Antibodies", (IRL Press Limited, Oxford, England) p. 59.

Roholt, O. et al., "Specific Combination of H and L Chains of Rabbit γ–Globulins", *Proc. Natl. Acad. Sci.,* 51: 173–178 (1964).

Rosselin, G., "The Receptors for the VIP Family Peptides (VIP, Secretin, GRF, PHI, PHM, GIP, Glucagon and Oxyntomodulin). Specificities and Identity.", *Peptides,* 7(Suppl. 1): 89–100 (1986).

Ruff, M. R. et al., "CD4 Receptor Binding Properties that Block HIV Infectivity cause Human Monocyte Chemotaxis", *FEBS Letters,* 211: 17–22 (1987).

Sacerdote, P. et al., "Vasoactive Intestinal Peptide 1–12. A Ligand for the CD4 (T4)/Human Immunodeficiency Virus Receptor", *J. of Neuroscience Res.,* 18: 102–107 (1987).

Sastry, L., et al., "Cloning of the immunological repertoire in *Escherichia coli* for generation of monoclonal catalytic antibodies", *Proc. Natl. Acad. Sci. U.S.A.,* 86: 5728–5732 (1989).

Schultz, P. G., "Catalytic Antibodies", *Acc. Chem. Res.,* 22: 287 (1989).

Schultz, P. G., "The Interplay Between Chemistry and Biology in the Design of Enzymatic Catalysts", *Science,* 240: 426 (1988).

Shenkin, P. S. et al., "Predicting Antibody Hypervariable Loop Conformation. I. Ensembles of Random Conformations for Ringlike Structures", *Biopolymers 26*: 2053 (1987).

Sheriff, S. et al., "Three–Dimensional Structure of an Antibody–Antigen Complex", *Proc. Natl. Acad. Sci. U.S.A.,* 84: 8075 (1987).

Shokat, K. M. et al., "A New Strategy for the Generation of Catalytic Antibodies", *Nature,* v.338, pp. 269–271 (Mar. 1989).

Skerra, A. et al., "Assembly of a Functional Immunoglobulin $F_v$ Fragment in *Escherichia coli*", *Science,* 240: 1038–1043 (1988).

Smith–Gill, S. J. et al., "Contributions of Immunoglobulin Heavy and Light Chains to Antibody Specificity for Lysozyme and Two Haptens", *J. Immunology,* 139: 4135 (1987).

Stewart, J. M. et al., "Solid Phase Peptide Synthesis", Pierce Chemical Co., Rockford, Illinois (1984).

Sun, L. K. et al., *Proc. Natl. Acad. Sci. U.S.A.,* 84: 214–218 (1987).

Tramontano, A. et al., "Specificity and Mechanism of Esterolytic Antibodies", *J. of Cellular Biochemistry,* Supp. 11C, Abstract N 417, p. 238 (1987).

Tramontano, A. et al., "Antibodies as Enzymic Catalysts", *J. Cellular Biochemistry,* Supp. 11C, p. 199, Abstract N 022 (1987).

Unkeless, J. C. et al., "Structure and Function of Human and Murine Receptors for IgG", *Ann. Rev. Immunology,* 6: 251–281 (1988).

Van Regenmortel, R. H. V., *Synthetic Peptides as Antigens,* Laboratory Techniques in Biochemistry and Molecular Biology Series (Editors R. H. Burdon and P. H. van Knippenberg), 19: 1–39 (1988).

Van der Eb, A. J. et al., "Assay of Transforming Activity of Tumor Virus DNA", *Meth. Enzymol.,* 65: 826–839 (1980).

Ward, E. S. et al., "Binding activities of a repertoire of single immunoglobulin variable domains secreted from *Escherichia coli*", *Nature,* 341: 544–546 (1989).

Winter, G. P., "Antibody Engineering", *Phil Trans. R. Soc. Lond.,* B 324, 537–547 (1989).

Woie, L. et al., "Increase in Plasma VIP in Muscular Exercise", *Gen. Pharmacol.,* 17: 321–326 (1987).

Wong, G. C. et al., "Human GM–CSF: Molecular Cloning of the Complementary DNA and Purification of the Natural and Recombinant Proteins", *Science,* 228: 810–815 (1985).

Yang, Y. C. et al., "Human IL–3 (Multi–CSF): Identification by Expression Cloning of a Novel Hematopoietic Growth Factor Related to Murine IL–3", *Cell,* 47: 3–10 (1986).

Yokota, T. et al., "Isolation and characterization of a human interleukin cDNA clone, homologous to mouse B–cell stimulatory factor 1, that expresses B–cell and T–cell stimulatory activities", *Proc. Natl. Acad. Sci. U.S.A.,* 83: 5894–5896 (1986) CA.

Edwards et al., "Human Monoclonal Antibodies and the Selection AF Antigens Suitable for Therapy" in *Monoclonal Antibodies '84: Biological and Clinical Applications: Proceedings of the International Symposium on Monoclonal Antibodies '84* held in Florence, Italy, Oct. 16–19, 1984.

Berchtold et al., *Blood* vol. 74, No. 7, pp. 2414–2417 (1989).

Nobeyuki et al., *Nature,* vol. 304, pp. 547–549 (1983).

INHIBITORS OF CATALYTIC ANTIBODIES

CROSS REFERENCE TO RELATED APPLICATION

This application is a continuation of application Ser. No. 08/009,915, filed on Jan. 27, 1993, now abandoned, which in turn is a divisional of application Ser. No. 07/486,594, filed on Feb. 28, 1990, now U.S. Pat. No. 5,194,585 issued on Mar. 10, 1993, which is a continuation-in-part of application Ser. No. 07/343,081, filed Apr. 25, 1989, now U.S. Pat. 5,236,836 issued on Aug. 17, 1993.

FIELD OF THE INVENTION

This invention pertains generally to substances capable of inhibiting catalytic antibodies and more particularly to substances capable of inhibiting naturally occurring catalytic autoantibodies.

Several publications are referenced in this application by Arabic numerals within parentheses in order to more fully describe the state of the art to which this invention pertains. Full citations for these references are found at the end of the specification immediately preceding the claims and the disclosures of these publications are expressly incorporated herein by reference.

BACKGROUND OF THE INVENTION

The nature of the forces involved in ligand binding by antibodies and substrate binding by enzymes is similar, viz., hydrogen bonding, electrostatic interaction and hydrophobic effect. The energy obtained from enzyme-substrate binding may be visualized to force electronic strain in the substrate and facilitate the formation of a transition state. There is strong evidence for the theory that enzymes bind the transition state of the reaction they catalyze better than the ground state, resulting in a reduced free energy of activation for the reaction (1). This has come to be known as the transition state theory of enzymatic catalysis. Other factors that may facilitate enzymatic catalysis are the proximity and orientation effects—apposition of correctly oriented reactants within the active site of the enzyme would reduce the requirement for a large number of random collisions prior to a productive reactant interaction. In principle, antibodies could catalyze chemical reactions by similar means.

The first report of chemical conversion of a ligand by an antibody appeared in 1980 (2), but the steroid ester hydrolysis by a rabbit polyclonal antiserum described in this report was stoichiometric rather than catalytic. Subsequently, antibodies have been demonstrated to catalyze or facilitate chemical reactions, including acyl transfer (3), pericyclic (4) and redox reactions (5). It is generally believed that these antibodies obtain their catalytic properties, like enzymes, from their ability to bind the transition state of the ligand better than its ground state.

The known catalytic antibodies include those generated by immunization with selected epitopes as described above, and those which have been shown to occur naturally (6). These naturally occurring antibodies are produced by an animal's immune system to the animal's own cellular component (self-antigen), hence "autoantibodies", as opposed to antibodies elicited with an antigen introduced by specific immunization against a target antigen, and are known to enhance the rate of a chemical reaction, e.g., the cleavage of a peptide bond.

Antibodies with enzymatic activity offer the possibility of specific, high efficiency catalytic chemical conversion of ligands. Many biological mediators are peptides or proteins, including the antigens of pathogenic organisms, hormones, neurotransmitters and tumor specific antigens. It should be possible to utilize the vast repertoire of specificities that the immune system encompasses to catalyze chemical reactions not within the scope of naturally occurring enzymes. The combination of antibody specificity with the catalytic power of enzymes has the potential of generating potent therapeutic agents, e.g., catalytic antibodies capable of specifically hydrolyzing key viral coat proteins, tumor specific proteins, or endogenous proteins involved in disease. The utilization of these catalytic antibodies in medicine and industry would be greatly enhanced if a specific, selective method of inhibiting the activity of these antibodies were also available.

For example, such inhibition could be useful in the treatment of autoimmune diseases. It is well known that certain autoimmune diseases are associated with autoantibodies directed against hormones and cell surface antigens. Examples of these diseases and associated autoantibodies are:

| Disease | Autoantibody to |
|---|---|
| Diabetes | Insulin, Insulin receptor |
| Myasthenia gravis | acetylcholine receptor |
| Graves disease | thyroid stimulating hormone receptor |
| Systemic lupus erythematosus | small nuclear RNA, DNA, histones |
| Pernicious anemia | Intrinsic factor of Castle, gastric parietal cell antibodies |

It is known to treat autoimmune diseases generally by means of non-specific anti-immune treatments. These known treatments include steroids, alkylating agents, radiation, plasmaphoresis, and surgical removal of the spleen. Each of these treatments suffers from many disadvantages well known in the art such as impairment of the patient's immune system. Since catalytic autoantibodies are likely to cause more harm than non-catalytic antibodies, it is now believed that the autoimmune diseases are caused by catalytic autoantibodies directed against nucleic acids, key regulatory peptides and proteins (e.g., insulin, glucagon, prolactin, VIP, substance P, blood clotting factors) and the cell surface receptors for these agents.

For example, asthma is believed to be caused by a deficiency of vasoactive intestinal peptide (VIP). VIP is a 28 amino acid peptide originally isolated from the intestine but now recognized to be a neuropeptide widely distributed in the central and peripheral nervous systems. There is evidence that VIP is a neurotransmitter in its own right. In addition, VIP may modulate neuroetransmission by classical transmitters and has been implicated in regulation of blood pressure, bronchial tone, neuroendocrine activity and exocrine secretion. VIP appears to be the major neurobronchodilator in humans and a diminished influence of VIP on the airways may permit a dominance of constrictor influences, and may underlie airway hyperactivity in asthma.

VIP belongs to a family of structurally related peptides, other prominent members of which are peptide histidine isoleucine (PHI), growth hormone releasing factor (GRF) and secretin. Like the peptides themselves, there is evidence that the receptors for VIP, GRF, PHI and secretin are related. Receptors for VIP are found in lung, vascular smooth muscle, brain, pancreas, skin, intestine and other tissues. The amino acid sequence of VIP is as follows:

H S D A V F T D N Y T R L R K Q M A V K Y L N S I L N-NH$_2$.

It has been discovered that VIP binding antibodies exist in human circulation (7–9). Immunoprecipitation with anti-human IgG as well as chromatography on DEAE-cellulose, gel filtration columns and immobilized protein-G indicate that the plasma VIP binding activity is largely due to IgG antibodies. The antibodies to VIP are present in the blood of 18% of asthma patients and 30% of healthy subjects with a history of habitual muscular exercise, compared to only 2% of healthy subjects with no such history. The antibodies are highly specific for VIP, judged by their poor reaction with peptides related to VIP (i.e., GRF, PHI and secretin). A clear difference in the VIP binding affinity of the antibodies from asthma patients (mean $K_{bind}$=0.13 Nm$^{-1}$) and healthy subjects (mean $K_{bind}$=7.7 Nm$^{-1}$) was observed—the antibodies from the asthmatics exhibiting a 60-fold greater binding affinity. The immune IgG from asthma patients reduces the binding of VIP by lung receptors as well as the VIP-responsive synthesis of cyclic AMP in lung membranes. Thus, the antibodies can be directed against an epitope(s) that binds the receptor or maintains the receptor-binding epitope in an active conformation.

These antibodies are detected by measuring their binding to porcine $^{125}$I-VIP. Human and porcine VIP are structurally identical (10). Thus, the porcine VIP-reactive antibodies found in asthma patients are autoantibodies. It had been observed that diabetics positive for plasma VIP-antibodies had been treated with insulin contaminated with VIP, suggesting that the formation of antibodies was related to the VIP contaminant (11).

The antigenic stimulus leading to formation of these autoantibodies cannot be identified with certainty. Candidate stimuli include exposure to viral determinants similar in sequence to VIP[e.g., Peptide-T, an epitope found on the human immunodeficiency virus (12)] and dietary ingestion of avian, fish and turtle VIP known to be structurally different from human VIP (13, 14). Muscular exercise, which results in increased plasma VIP immunoreactivity (15, 16), could also be a potential stimulus for VIP autoantibody formation. Indeed, asthma and muscular exercise appear to be associated with an increased incidence of autoantibodies directed against VIP.

Irrespective of the type of antigenic stimulation leading to VIP-autoantibody formation, these antibodies may produce important biologic changes. The range of $K_a$ values observed for the autoantibodies of asthma patients is similar to that reported for VIP receptors present in the lung and other tissues (17, 18), and these antibodies neutralize VIP receptor binding. It is possible that VIP-autoantibodies found in asthmatics neutralize the effect of VIP in the airways.

It has been discovered that these VIP autoantibodies catalyze the hydrolysis of VIP between amino acid residues 16 and 17, i.e. between glutamine (Gln$^{16}$) and methionine (Met$^{17}$). These are described in U.S. application Ser. No. 342,081, filed Apr. 25, 1989, the disclosure of which is incorporated herein by reference.

Thus, specific inhibitors of catalytic autoantibodies, e.g., an inhibitor of the autoantibody which catalyzes the cleavage of VIP, would provide an important therapeutic advance for the treatment of catalytic autoantibody autoimmune disease, in particular asthma and similar respiratory diseases. More generally, inhibitors of catalytic antibodies would provide the art with the means to tailor and control the catalytic activity of such antibodies, regardless of how they are used.

OBJECTS OF THE INVENTION

It is a general object of the invention to provide inhibitors of catalytic antibodies.

It is another object of the invention to provide inhibitors of catalytic autoantibodies.

It is another object of the invention to provide a method for inhibiting a catalytic antibody or autoantibody from catalyzing a chemical reaction of a substrate.

It is a further object of the invention to provide a method for treating an autoimmune disease in an animal wherein an autoantibody, which catalyzes a chemical reaction of a substrate in the animal, contributes to or is responsible for the pathophysiology of the autoimmune disease as a result of the reaction being catalyzed, by administering to the animal an inhibitor of the autoantibody.

It is another object of the invention to provide a method of treating asthma and bronchitis by administering to an animal afflicted with these diseases a vasointestinal peptide (VIP) homolog which is an inhibitor of a catalytic anti-VIP autoantibody.

It is still another object of the invention to provide a naturally occurring inhibitor which can be separated from naturally occurring catalytic autoantibodies.

These and other objects, features, and advantages of the invention will become readily apparent from the ensuing description, and the novel features will be particularly pointed out in the appended claims.

SUMMARY OF THE INVENTION

The invention is broadly directed to inhibitors of catalytic antibodies and methods of making and using the inhibitors. Thus, in one aspect the invention is directed to an inhibitor which inhibits an antibody from catalyzing a chemical reaction of a substrate, the inhibitor comprising (a) a fragment of the substrate, (b) an analog of a fragment of the substrate or (c) an analog of the substrate, provided that the inhibitor was not used to elicit the catalytic antibody.

In another aspect, the invention is directed to an inhibitor which inhibits an autoantibody from catalyzing a chemical reaction of a substrate.

In still another aspect, the invention is directed to an inhibitor which inhibits a first antibody from catalyzing a chemical reaction of a substrate, the inhibitor comprising a second antibody which is antiidiotypic to the first antibody.

Another aspect of the invention is directed to an inhibitor capable of inhibiting anti-VIP catalytic autoantibody from catalyzing the cleavage of the Gln$^{16}$-Met$^{17}$ peptide bond in VIP which comprises VIP[22–28].

The invention also concerns methods for preparing inhibitors of catalytic antibodies. Thus, in one embodiment, the invention is directed to a method for preparing an inhibitor which inhibits an antibody from catalyzing a chemical reaction of a substrate but which is not itself an antigen capable of eliciting the antibody. The method comprises the steps of synthesizing one or more fragments of the substrate; or synthesizing one or more analogs of one or more fragments of the substrate; or synthesizing one or more analogs of the substrate; and screening the fragment(s) or analog(s) synthesized in steps (a)–(c) to identify a fragment(s) or analog(s) which inhibits the antibody.

In another embodiment, the invention is a method for preparing an inhibitor which inhibits an autoantibody from catalyzing a chemical reaction of a substrate. The method comprises the steps of collecting serum from an animal having the autoantibody; separating the gamma globulin fraction from the serum; separating from the gamma globulin fraction molecules which bind to the gamma globulin; and screening the molecules to identify a molecule(s) which is capable of inhibiting the autoantibody.

In still another embodiment, the invention is a method for preparing an inhibitor which inhibits an autoantibody from catalyzing the cleavage or formation of a bond contained in a substrate. The method comprises the steps of synthesizing one or more analogs or one or more fragments of the substrate and screening the analog(s) or fragment(s) to identify an analog(s) or fragment(s) which inhibits the autoantibody.

Another embodiment of the invention is directed to a method for preparing an inhibitor which inhibits a first antibody from catalyzing a chemical reaction of a substrate. The method comprises the steps of generating a plurality of antibodies to the first antibody and screening the plurality of antibodies so generated to identify a second antibody which is capable of binding to and thereby inhibiting the first antibody, the second antibody being antiidiotypic to the first antibody.

The invention also concerns inhibitors having been prepared by the methods described above. Accordingly, in one embodiment, the invention is directed to an inhibitor which inhibits an antibody from catalyzing a chemical reaction of a substrate, the inhibitor having been prepared by a process comprising the steps of synthesizing one or more fragments of the substrate; or synthesizing one or more analogs of one or more fragments of the substrate; or synthesizing one or more analogs of said substrate; and screening said fragment(s) or analog(s) synthesized in steps (a)–(c) to identify a fragment(s) or analog(s) which inhibits said antibody, provided that said inhibitor is not an antigen capable of eliciting said catalytic antibody.

In another embodiment, the invention is directed to an inhibitor which inhibits an autoantibody from catalyzing a chemical reaction of a substrate, the inhibitor having been prepared by a process comprising the steps of collecting serum from an animal having the autoantibody; separating the gamma globulin fraction from the serum; separating from the gamma globulin fraction molecules which bind to the gamma globulin; and screening the molecules to identify a molecule(s) which is capable of inhibiting the autoantibody.

In another aspect, the invention is directed to an inhibitor which inhibits anti-VIP catalytic autoantibody from catalyzing the cleavage of the $Gln^{16}$-$Met^{17}$ peptide bond in VIP, the inhibitor having been prepared by a process comprising the steps of collecting serum from an animal having anti-VIP catalytic autoantibody, separating the gamma globulin fraction from the serum; separating from the gamma globulin fraction molecules which bind to the gamma globulin; and screening the molecules to identify a molecule(s) which is capable of binding to and thereby inhibiting the anti-VIP catalytic autoantibody from catalyzing the rate of cleavage of the $Gln^{16}$-$Met^{17}$ peptide bond in VIP.

Another embodiment of the invention is directed to an inhibitor which inhibits an autoantibody from catalyzing a chemical reaction of a substrate, the inhibitor having been prepared by a process comprising the steps of synthesizing one or more analogs or one or more fragments of the substrate and screening the analog(s) or fragment(s) to identify an analog(s) or a fragment(s) which inhibits the autoantibody.

The invention is also directed to an inhibitor which inhibits a first antibody from catalyzing a chemical reaction of a substrate, the inhibitor comprising a second antibody which is antiidiotypic to the first antibody, the second antibody having been prepared by a process comprising the steps of generating a plurality of antibodies to the first antibody and screening the plurality to identify a second antibody which is capable of binding to and thereby inhibiting the first antibody.

The invention also concerns methods for using inhibitors to inhibit antibodies and/or autoantibodies from catalyzing a chemical reaction of a substrate. Thus, the invention is directed to a method for inhibiting an antibody from catalyzing a chemical reaction of a substrate comprising contacting the antibody with an effective amount of inhibitor under conditions suitable for the inhibition to take place, the inhibitor having been prepared by a process comprising the steps of:

(a) synthesizing one or more fragments of the substrate; or (b) synthesizing one or more analogs of one or more fragments of the substrate; or (c) synthesizing one or more analogs of said substrate; and (d) screening the fragment(s) or analog(s) synthesized in steps (a)–(c) to identify a fragment(s) or analog(s) which inhibits the antibody, provided that the inhibitor is not an antigen capable of eliciting the catalytic antibody.

In another embodiment, the invention is directed to a method for inhibiting an autoantibody from catalyzing a chemical reaction of a substrate comprising contacting the autoantibody with an effective amount of an inhibitor under conditions suitable for the inhibition to take place, the inhibitor having been prepared by a process comprising the steps of:

(a) collecting serum from an animal having the autoantibody;

(b) separating the gamma globulin fraction from the serum;

(c) separating from the gamma globulin fraction molecules which bind to the gamma globulin; and (d) screening the molecules to identify a molecule(s) which is capable of inhibiting the autoantibody.

Another embodiment of the invention is directed to a method for inhibiting an autoantibody from catalyzing a chemical reaction of a substrate comprising contacting the autoantibody with an effective amount of an inhibitor under conditions suitable for the inhibition to take place, the autoantibody having been prepared by a process comprising the steps of:

(a) synthesizing one or more analogs or one or more fragments of the substrate; and (b) screening the analog(s) or fragment(s) to identify an analog(s) or a fragment(s) which inhibits the autoantibody.

In still another embodiment, the invention is directed to a method for inhibiting a first antibody from catalyzing a chemical reaction of a substrate comprising contacting the first antibody with an effective amount of a second antibody under conditions suitable for the inhibition to take place, the second antibody being antiidiotypic to the first antibody, the second antibody having been prepared by a process comprising the steps of:

(a) generating a plurality of antibodies to the first antibody; and (b) screening said plurality to identify the second antibody which is capable of binding to and thereby inhibiting the first antibody.

The invention also concerns methods for using inhibitors of autoantibodies to treat autoimmune disease. Thus, in one embodiment, the invention is directed to a method for treating autoimmune disease in an animal wherein an autoantibody, which catalyzes a chemical reaction of a substrate in the animal, contributes to or is responsible for the pathophysiology of the autoimmune disease as a result of the reaction being catalyzed. The methods comprises the step of administering to the animal or to a fluid of the animal an inhibitor which inhibits the autoantibody from catalyzing the chemical reaction.

In another embodiment, the invention is directed to a method for treating autoimmune disease in an animal wherein an autoantibody, which catalyzes a chemical reaction of a substrate in the animal, contributes to or is responsible for the pathophysiology of the autoimmune disease as a result of the reaction being catalyzed. The method comprises the steps of synthesizing one or more fragments of the substrate; or synthesizing one or more analogs of one or more fragments of the substrate; or synthesizing one or more analogs of said substrate; or screening said fragment(s) or analog(s) synthesized in steps (a)–(c) to identify a fragment(s) or analog(s) which inhibits said autoantibody; and administering said inhibitor to an animal afflicted with said autoimmune disease or to a fluid of said animal.

Another embodiment of the invention is directed to a method for treating autoimmune disease in an animal wherein an autoantibody, which catalyzes a chemical reaction of a substrate in the animal, contributes to or is responsible for the pathophysiology of the autoimmune disease as a result of the reaction being catalyzed. The method comprises the steps of collecting serum from an animal having said autoantibody; separating the gamma globulin fraction from said serum; separating from the gamma globulin fraction molecules which bind to the gamma globulin; screening the molecules to identify a molecules(s) which is capable of binding to and thereby inhibiting said autoantibody from catalyzing the chemical reaction of the substrate; and administering a molecule(s) identified in step (d) to an animal afflicted with said autoimmune disease or to a fluid of said animal.

In still another embodiment, the invention is directed to a method for treating autoimmune disease in an animal wherein an autoantibody, which catalyzes a chemical reaction of a substrate in the animal, contributes to or is responsible for the pathophysiology of the autoimmune disease as a result of the reaction being catalyzed. The method comprises administering to the animal or to a fluid of the animal an inhibitor which inhibits the autoantibody from catalyzing the chemical reaction, the inhibitor having been prepared by a process comprising the steps of synthesizing one or more fragments of the substrate; or synthesizing one or more analogs of one or more fragments of the substrate; or synthesizing one or more analogs of the substrate; and screening said fragment(s) or analog(s) synthesized in steps (a)–(c) to identify a fragment(s) or an analog(s) which inhibits said autoantibody.

Another embodiment of the invention is directed to a method for treating autoimmune disease in an animal wherein an autoantibody, which catalyzes a chemical reaction of a substrate in the animal, contributes to or is responsible for the pathophysiology of the autoimmune disease as a result of the reaction being catalyze. The method comprises the step of administering to an animal afflicted with the autoimmune disease or to a fluid of the animal an inhibitor which inhibits the autoantibody from catalyzing the chemical reaction, the inhibitor having been prepared by a process comprising the steps of collecting serum from an animal having said autoantibody; separating the gamma globulin fraction from said serum; separating from the gamma globulin fraction molecules which bind to the gamma globulin; and screening the molecules to identify a molecule(s) which is capable of binding to and thereby inhibiting said autoantibody from catalyzing the chemical reaction of the substrate.

Another aspect of the invention is directed to a pharmaceutical composition for treating autoimmune disease in an animal wherein an autoantibody, which catalyzes a chemical reaction of a substrate in the animal, contributes to or is responsible for the pathophysiology of the autoimmune disease as a result of the reaction being catalyzed. The composition comprises an inhibitor which inhibits the autoantibody from catalyzing the chemical reaction and a pharmaceutically suitable carrier.

In still another aspect, the invention is directed to a pharmaceutical composition for treating asthma which comprises an inhibitor which inhibits anti-VIP catalytic autoantibody from catalyzing the cleavage of the $Gln^{16}$-$Met^{17}$ peptide bond in VIP, said inhibitor having been prepared by a process comprising the steps of collecting serum from an animal having anti-VIP catalytic autoantibody; separating the gamma globulin fraction from the serum; separating from the gamma globulin fraction molecules which bind to the gamma globulin; and screening the molecules to identify a molecule(s) which is capable of binding to and thereby inhibiting the autoantibody from catalyzing the rate of cleavage of the $Gln^{16}$-$Met^{17}$ peptide bond in VIP, and a pharmaceutically suitable carrier.

Yet another aspect of the invention is directed to a pharmaceutical composition for treating asthma which comprises VIP[22–28] and a pharmaceutically suitable carrier therefor.

BRIEF DESCRIPTION OF THE DRAWINGS

The invention will be understood more clearly and fully from the following detailed description, when read with reference to the accompanying figures, in which:

FIGS. 7 and 8 show the amino acid sequences of the VIP fragments determined by the Edman degradation method;

DETAILED DESCRIPTION OF THE INVENTION

Figure 1:
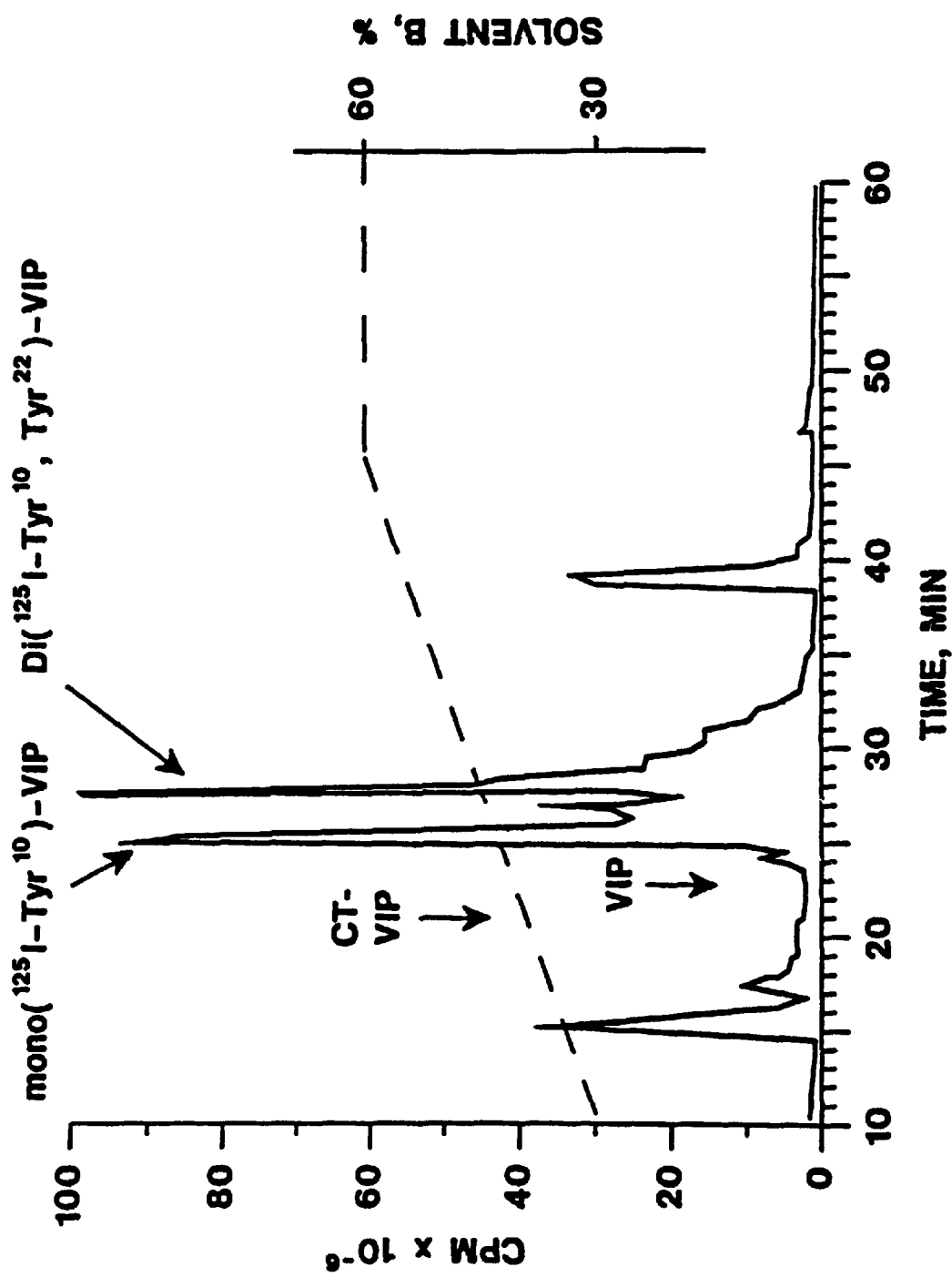
FIG. 1 shows the separation of mono ($^{125}I$, $Tyr^{10}$)-VIP and di($^{125}I$, $Tyr^{10}$, $Tyr^{22}$)-VIP by reverse phase HPLC.

The invention is broadly directed to inhibitors which are capable of inhibiting catalytic antibodies from catalyzing a chemical reaction. "Catalytic antibody" as used herein is a substance which is capable of changing the rate of a chemical reaction, all other conditions (e.g., temperature, reactant/substrate concentration, etc.) being the same and which does not enter into the chemical reaction and, therefore, is not consumed in the reaction. It is also a substance which exhibits the capability of converting multiple moles of reactant/substrate per mole of catalytic antibody; and which, from a mechanistic viewpoint, binds the reactant/substrate, effects the accelerated conversion of the reactant/substrate to the product and then releases the product; and which changes the rate of the chemical reaction without shifting the position of the equilibrium. While the aforementioned definitions are characteristics of ideal catalysts, in practice, even the best of catalysts become poisoned or deactivated by contamination in the reaction system or as a result of chemical or physical destruction during the reaction process. For reasons well-known in the art, the true operation of a catalyst may be obscured by components of the reaction system or by the condition of the reaction environment.

The art has adopted certain working definitions to express catalytic activity. These expressions are [1] $k_{cat}$, or "turnover" and [2] $k_{cat}/k_{uncat}$, the "rate enhancement factor". Turnover indicates the number of molecules of reactant/substrate which can be converted to product per mole of catalytic antibody per unit time. For example, if a molecule exhibits a turnover of $10^3$ of substrate per minute and the molecule maintains its catalytic activity for 24 hours at room temperature and at its optimal pH, each molecule of catalyst would then make a total of $1.4 \times 10^6$ conversions, indicating its catalytic behavior. This total conversion is to be distinguished from the total conversion in a stoichiometric reaction, which will never exceed 1.0, no matter how long the reaction is carried out. The rate enhancement factor is a dimensionless number which expresses the rate of reaction in the presence of catalyst to the rate of reaction in the absence of catalyst, all other reaction conditions being equal.

In accordance with the invention, an antibody can comprise purified immunoglobulins (IgG, IgM, IgA, IgD or IgE) or antibody fragments, such as, for example, Fab, F(ab')$_2$, Fv, etc., of immunoglobulins. Catalytic antibodies include two major categories. The first category includes catalytic antibodies which have been rationally designed, i.e., antibodies elicited with an antigen introduced by specific immunization against a target antigen or substrate. Such catalytic antibodies, processes for their preparation and their use are described in U.S. Pat. No. 4,888,281, issued Dec. 19, 1989, U.S. Pat. No. 4,792,446, issued Dec. 20, 1988 and U.S. application Ser. No. 064,239, filed Jun. 19, 1987, all of the disclosures of which are incorporated herein by reference. The other category of catalytic antibodies includes naturally occurring antibodies which are produced by an animal's immune system to the animal's own cellular component (self-antigen), as opposed to the first category of catalytic antibodies previously described. These "autoantibodies" are described in U.S. application Ser. No. 343,081, filed Apr. 25, 1989, the disclosure of which is incorporated herein by reference.

An inhibitor in accordance with the invention prevents a catalytic antibody from catalyzing a chemical reaction of a substrate. The inhibitor binds to the catalytic antibody, thereby preventing the catalytic antibody from binding to the substrate and catalyzing the reaction of the substrate.

The term "chemical reaction" refers to a reaction wherein at least one reactant is converted to at least one product. Such chemical reactions include chemical reactions which can be catalyzed by enzymes such as, for example, oxoreductases, transferases, hydrolases, lyases, isomerases and ligases, as well as chemical reactions for which no catalytic enzymes are known such as, for example, oxidations, reductions, additions, condensations, eliminations, substitutions, cleavages and rearrangements. In one embodiment of the invention, the chemical reaction is the cleavage of a peptide bond. Peptide bond as used herein refers to an amide bond linking two adjacent amino acid residues and is generically represented by the following formula wherein the peptide bond is shown within the box:

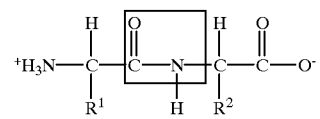

An amino acid consists of a carbon atom to which is bonded an amino group, a carboxyl group, a hydrogen atom and a distinctive group referred to as a "side chain" ($R_1$ and $R_2$ in the formula above). Amino acid as used herein includes the twenty naturally occurring amino acids which comprise the building blocks of proteins. It is understood by those skilled in the art that when either of the adjacent amino acids is proline, the respective side chains $R_1$ or $R_2$ are bonded to the adjacent nitrogen atoms to form the characteristic 5-membered proline ring.

The term "substrate" is synonymous with the reactant in the chemical reaction and can be any of a number of molecules and biomolecules including but not limited to peptides, proteins, phospholipids, carbohydrates (e.g., glycogen, glucose, etc.) and drugs (including abused substances and drugs from exogenous sources). In one embodiment, the substrate contains a peptide bond or bonds to be cleaved and can be any proteinaceous molecule, such as, for example, a regulatory protein or a structural protein including but not limited to peptide hormones (e.g., insulin, growth hormone, secretin, etc.), peptide neurotransmitters, neuromodulators and neurohumoral factors (e.g., VIP, endorphins, enkephlins, bradykinins, substance P., etc.), tumor proteins (e.g., oncogene products, carcinoembryonic antigens, etc.), bacterial proteins and viral proteins (e.g., human immunodeficiency viral (HIV) gp 120 influenza glycoproteins, etc.). In another embodiment, the substrate can be a self-antigen, i.e., any antigen which the body makes using its own genetic code. Thus, self-antigens are distinguished from foreign antigens (e.g., bacterial, viral antigens). The term "animal" as used herein refers to any organism with an immune system and includes mammalian and non-mammalian animals.

In accordance with one embodiment of the invention, an inhibitor can comprise a fragment of the substrate, an analog of a fragment of the substrate or an analog of the substrate provided that, in the case of catalytic antibodies elicited by specific immunization within an antigen, the inhibitor is not an antigen capable of eliciting the catalytic antibody. The term "fragment of the substrate" refers to a molecule which represents some portion of the substrate. For example, if the substrate is a peptide, the inhibitor can be a fragment of the peptide, e.g., one or more homologous peptides having amino acid residues which are identical to amino acid residues in one or more portions of the peptide substrate. The term "analog" is used in its broadest sense and includes isomers, homologs or any molecule which sufficiently resembles the substrate in terms of chemical structure such that an antibody raised against the analog may participate in an immunological reaction with the substrate but will not necessarily catalyze a reaction of the analog. For example, an analog of the substrate can be a molecule which is structurally similar to the substrate but differs from the substrate by one or more elements of the same valance and group of the periodic table as the element or elements replaced in the substrate, e.g., an analog of the transition state of the reaction to be catalyzed. An analog of the substrate in accordance with the invention can also be an optical antipode of the substrate. For example, if the substrate is a D-amino acid, an inhibitor in accordance with the invention would be the L-optical antipode. In the case of an autoantibody where the substrate is a self-antigen, an inhibitor of the autoantibody can be an analog of the self-antigen, a small peptide containing an epitope of the self-antigen at which epitope the chemical reaction does or does not take place, an analog of a small peptide containing the epitope, or a small peptide containing an analog of the epitope. The above-described inhibitors can be synthesized by a variety of chemical and immunological biosynthetic methodologies well-known in the art (19).

Another embodiment of the invention is directed to an inhibitor comprising an antibody which is antiidiotypic to the antibody to be inhibited. An antibody that is "antiidiotypic" refers to an antibody that binds to a second antibody on the variable region of the second antibody. Such an inhibitor is prepared by generating a plurality of antibodies to the catalytic antibody and screening the plurality to identify an antiidiotypic antibody which is capable of binding to and thereby inhibiting the catalytic antibody. Methods for the generation of the plurality of antibodies and screening assays for binding and inhibition are well-known in the art. In a preferred embodiment, an animal is immunized with the catalytic antibody to generate antibody-producing lymphocytes in the animal which are then removed from the animal and fused with myeloma cells to produce a plurality of hybridoma cells each in turn producing monoclonal antibodies. The monoclonal antibodies can then be screened for binding to and inhibition of the target catalytic antibody by methods well-known in the art (6).

The hydrolytic activity of anti-VIP catalytic autoantibody is latent because of the presence of a tightly bound, relatively small sized inhibitor. This latency was based on the discovery that little or no VIP hydrolytic activity was present in the IgG fraction of serum isolated from individuals having the anti-VIP catalytic autoantibody when the IgG was tested for hydrolytic activity directly after purification on immobilized protein G (6). However, VIP hydrolytic activity was observed when the IgG was subjected to any of the following treatments: (a) extensive dialysis; (b) two cycles of ultrafiltration; (c) prolonged washing of the IgG at neutral pH when bound on protein G-Sepharose; or (d) affinity chromatography on a VIP-Sepharose column.

The binding of an antigen (or an inhibitor) to an antibody is an equilibrium reaction as follows:

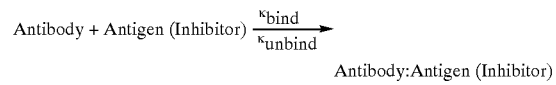

Antibody:Antigen (Inhibitor)

Treatments (a)–(d) remove unbound inhibitor forcing the equilibrium to the left ($k_{unbind}$) and facilitating further removal of inhibitor, and thereby leaving behind hydrolytically active antibody.

Thus, in still another embodiment, the invention is directed to naturally occurring inhibitors of catalytic autoantibodies. The inhibitor is prepared by collecting serum from an animal having the target catalytic autoantibody, separating the gamma globulin fraction from the serum, separating from the gamma globulin fraction molecules which bind to the gamma globulin and screening the molecules so separated to identify a molecule which is capable of inhibiting the catalytic activity of the target autoantibody. These molecules include metal ions, antibodies, antibody fragments, etc. and are typically low molecular weight molecules ranging in weight from 1,000 to 15,000 Daltons.

In one embodiment, the molecules are separated from the gamma globulin fraction by ultrafiltration or by dialysis. The term "ultrafiltration" as used herein refers to a process for separating proteins from small molecules whereby pressure or centrifugal force is used to filter a liquid medium and small solute molecules through a semipermeable membrane having pores with an average cut-off molecular weight ranging from 1000 to 10,000 Daltons. Thus, for example, ultrafiltering an immunoglobulin with a molecular weight of 150,000 Daltons on a membrane with pores having an average cut-off molecular weight of 10,000 Daltons will cause molecules with molecular weights smaller than 10,000 Daltons to pass through the membrane into the ultrafiltrate while the immunoglobulin remains on the membrane. Accordingly, potential inhibitors will be found in the ultrafiltrate. The ultrafiltrate is then partially purified and fractions thereof are then screened for binding and inhibitory activity. Fractions showing inhibitory activity are subjected to further separation procedures in order to yield the pure inhibitor. Once isolated, the pure inhibitor is subjected to amino acid analysis and peptide sequencing and/or to other types of chemical analysis in order to identify the chemical structure.

The term "dialysis" as used herein refers to a process for separating globular proteins in solution from low-molecular weight solutes which utilizes a semipermeable membrane to retain protein molecules and allow small solute molecules and water to pass through. Dialysis membranes with molecular weight cut-offs ranging from 12,000–15,000 Daltons are advantageously used. Potential inhibitors in the dialysate are then screened for inhibitory activity and purified in a manner analogous to that described above with reference to ultrafiltration.

In another embodiment, molecules which bind to the gamma globulin are separated by washing after immobilization of the IgG on a non-specific protein support or by affinity chromatography on a protein support which is specific for the particular antibody for which an inhibitor is being sought. An example of a non-specific protein support is Protein G-Sepharose. Protein G-Sepharose will bind the $F_c$ region of all antibodies. Thus, in the case of anti-VIP catalytic autoantibody, Protein G-Sepharose will bind $F_c$ region of all antibodies in the sample as well as the $F_c$ region of the anti-VIP catalytic autoantibody. Once the IgG in the sample is immobilized, it is then washed with buffer to remove putative inhibitors. The putative inhibitors are then screened for inhibitory activity and purified in a manner analogous to that described above. The column is then washed with an acidic solution to release the free, activated IgG.

Affinity chromatography involves the use of a protein support which is specific only for the particular antibody for which an inhibitor is being sought because it will bind only to the variable region (i.e., antigen binding region) of the antibody. Affinity chromatography forces the antibody-inhibitor binding equilibrium in the direction of dissociation of the inhibitor because there is a competition between the inhibitor and the specific protein for the binding site on the antibody. Thus, affinity chromatography provides for the isolation of active site-directed inhibitors and, therefore, requires less washing to remove putative inhibitors than is required with the non-specific protein support described above. The putative inhibitors are then screened for inhibitor activity and purified in a manner analogous to that described above. The column is then washed with an acidic solution to release the free, activated IgG. In the case of anti-VIP catalytic autoantibody, a VIP-Sepharose column is advantageously used.

The inhibitors of the invention can then be used to inhibit a catalytic antibody from catalyzing the rate of a chemical reaction of a substrate. The catalytic antibody is contacted with an effective amount of the inhibitor under conditions suitable for the inhibition to take place. Suitable conditions for inhibition are any conditions which allow binding of the inhibitor to the target catalytic-antibody. Typically these conditions are physiologic conditions, i.e., conditions found in vivo (e.g., in the blood).

As noted above, it is well-known that certain autoimmune diseases are associated with autoantibodies directed against hormones and cell surface antigens. In autoimmune diseases where an autoantibody contributes to or is responsible for the pathophysiology of the disease as a result of catalyzing a reaction of a substrate, a methodology for treating autoimmune disease presents itself based on the use of an inhibitor, in accordance with the invention, of that autoantibody. Thus, another embodiment of the invention is directed to a method for treating autoimmune disease in an animal wherein an autoantibody, which catalyzes a chemical reaction of a substrate in the animal, contributes to or is responsible for the pathophysiology of said autoimmune disease as a result of the reaction being catalyzed. The method comprises administering to an animal afflicted with the autoimmune disease or to a fluid of such an animal an inhibitor in accordance with the invention which inhibits the autoantibody from catalyzing the chemical reaction. In a preferred embodiment, the inhibitor is administered directly to the animal as a pharmaceutical composition comprising the inhibitor and a suitable pharmaceutical carrier, either orally or by injection (I.V. or I.M.). In another preferred embodiment, the inhibitor is administered to the animal extracorporeally; i.e., a fluid of the animal, e.g., blood, is passed from the animal's body through a matrix which is impregnated with an inhibitor according to the invention. The autoantibody associated with the pathophysiology of the autoimmune disease is removed from the fluid as a result of binding between the inhibitor and the autoantibody, and the fluid is then returned to the body of the animal. Autoimmune diseases which can be treated in accordance with the invention include asthma, bronchitis, diabetes and impotence.

DESCRIPTION OF CERTAIN PREFERRED EMBODIMENTS

Certain preferred embodiments of the invention are directed to inhibitors of an autoantibody ("anti-VIP catalytic autoantibody") which catalytically cleave the peptide bond between glutamine and methionine ("$Gln^{16}$-$Met^{17}$") in VIP. In one embodiment, inhibitors are a family of peptide homologs of VIP which bind to the anti-VIP catalytic autoantibody without themselves undergoing catalytic cleavage.

Figure 11:
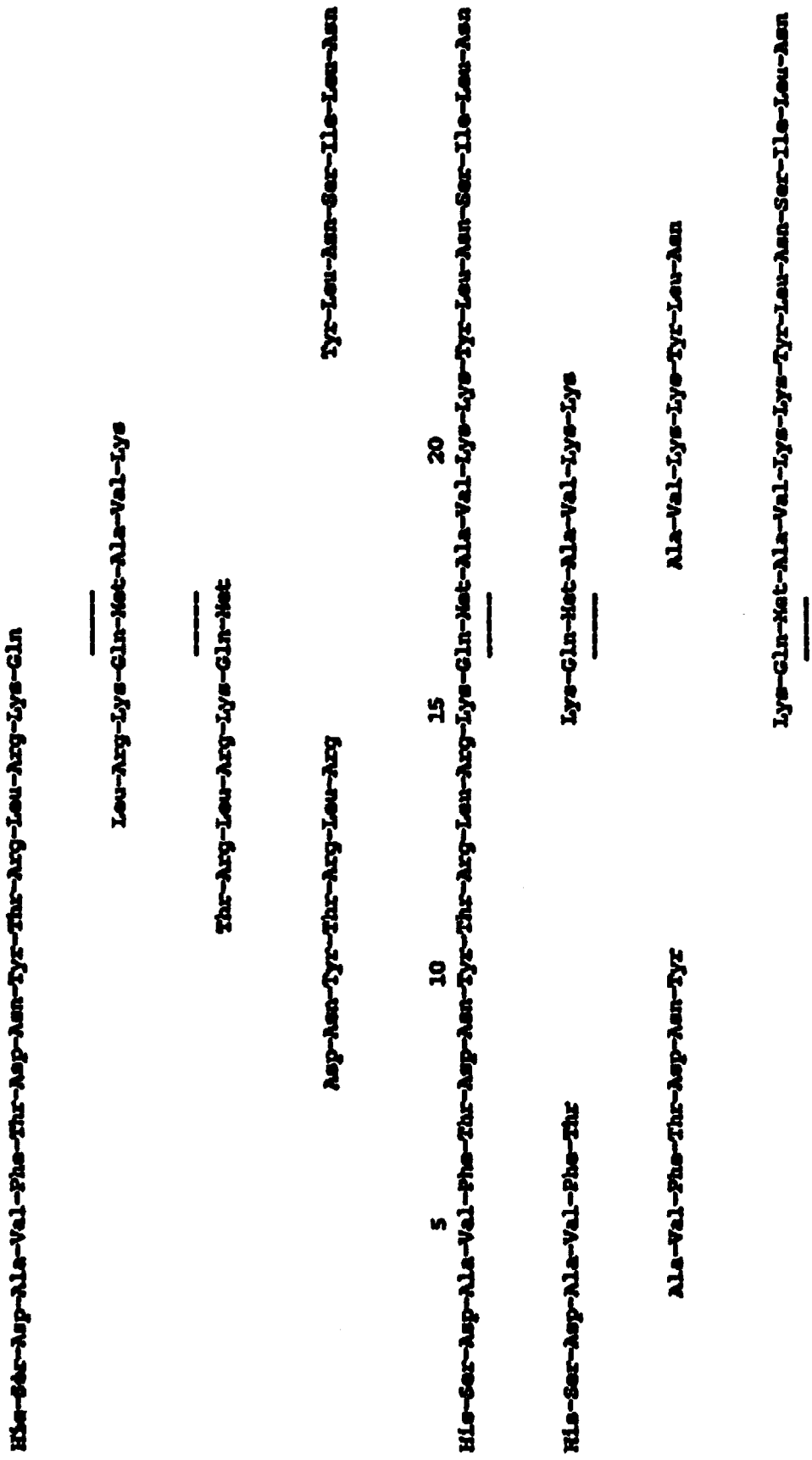
FIG. 11 shows ten synthetic VIP homologs (fragments) and the full 28 amino acid sequence of VIP (with five syntheyic VIP sequences being positioned in the figure above the full VIP sequence and five synthetic VIP homolog sequences being positioned in the figure below the full VIP sequence); wherein (---) denotes the bond cleaved (scissile bond) by anti-VIP catalytic autoantibody.
Figure 12:
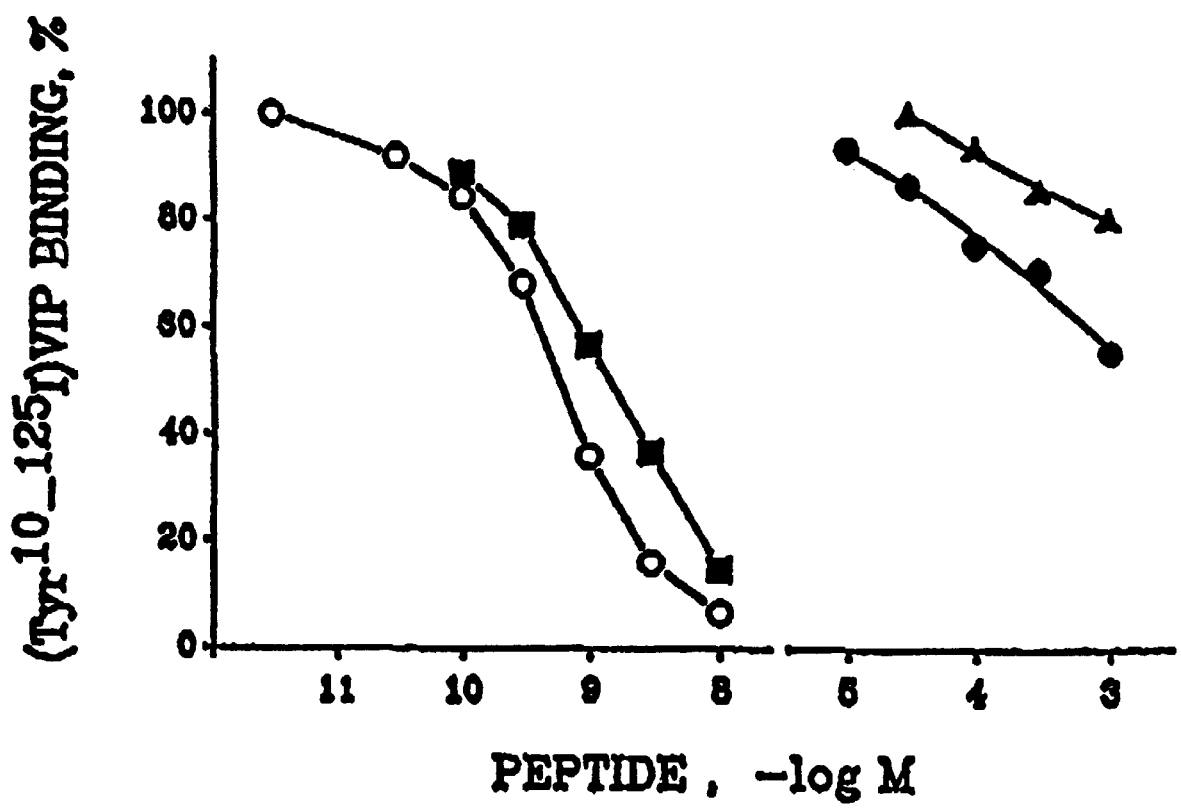
FIG. 12 shows saturable ($Tyr^{10}$-$^{125}I$)-VIP binding by the autoantibody fraction (100 μg purified IgG): Competitive inhibition by VIP(○), VIP[15–28] (■), VIP[22–28](●), and VIP[18–24] (▲)

Thus, ten synthetic peptide homologs (fragments of VIP) (FIG. 11), corresponding to linear subsequences of VIP, were screened for their reactivity with ($Tyr^{10}$-$^{125}I$) VIP binding autoantibody. IgG purified from the plasma of a human subject was the source of the antibody. The binding screens were performed using: (1) IgG which had not been dialyzed to remove the putative inhibitor of hydrolysis; (2) a temperature of 4° C.; or (3) buffer (7.5 mM sodium phosphate, pH 7.4, 0.64% sodium chloride, 0.5% bovine serum albumin, 25 mM EDTA, 0.005% bacitracin, 0.005% protamine sulfate, 0.073% sodium azide and 0.025% Tween-20), i.e., experimental conditions non-permissive for ($Tyr^{10}$-$^{125}I$)VIP hydrolysis. The N-terminal fragment VIP[1–16] at 500 μM failed to inhibit binding of ($Tyr^{10}$-$^{125}I$)VIP. The C-terminal fragment VIP[15–28], in contrast, inhibited the binding with potency ($K_I$ 1.25 nM) close to that of the full length peptide, VIP[1–28]($K_D$ 0.3 nM) (FIG. 12). Of the seven shorter peptides tested initially at a concentration of 500 μM each, only VIP[22–28] and VIP[18–24] inhibited ($Tyr^{10}$-$^{125}I$)-VIP binding. The $K_I$ for VIP[22–28] was 242 μM. VIP[22–28] showed approximately 8-fold greater potency than VIP[18–24]. Therefore, the reactivity of the latter peptide is believed to be due to the shared sequence VIP[22–24]. The apparent binding energy for the peptides were, in kcal/mole, VIP[1–28], 12.1; VIP[15–28], 11.3; and, VIP[22–28], 4.6. The binding energy of residues 22–28 is substantial, although it is only 38% of that for the full length peptide.

Figure 13:
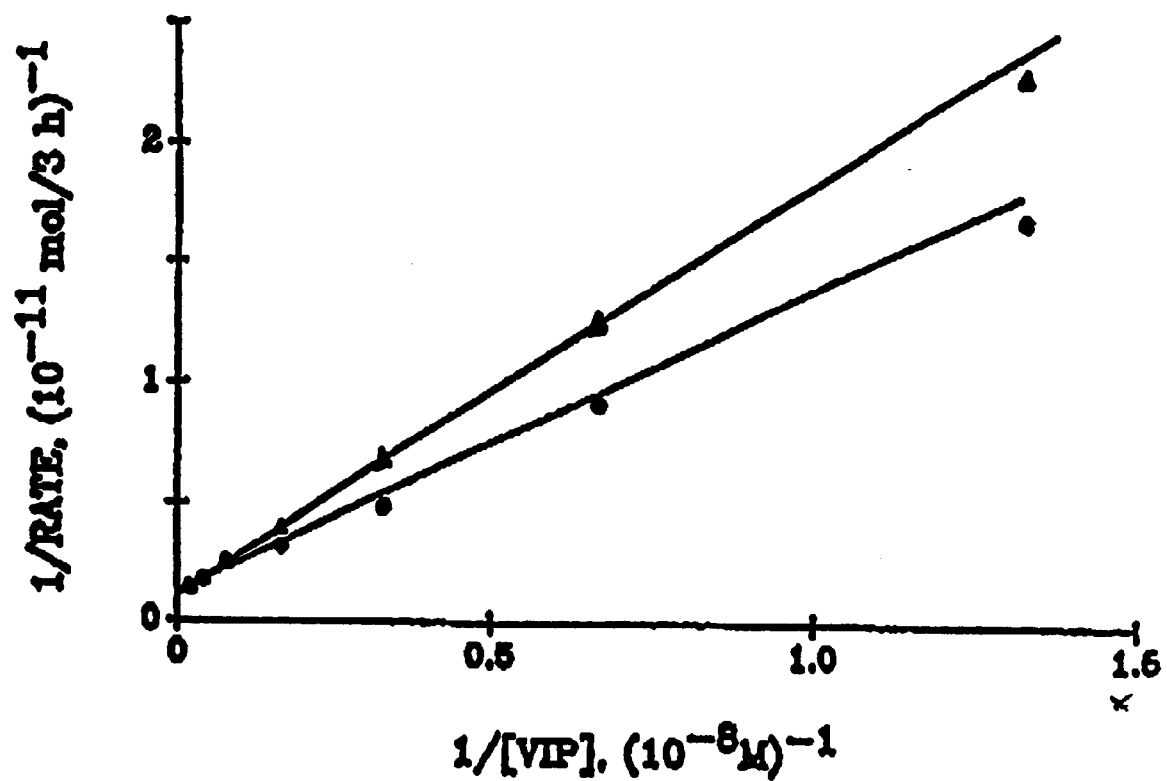
FIG. 13 shows catalytic hydrolysis of VIP[1–28] by the autoantibody (50 μg IgG): Inhibition by 100 μM VIP [22–28], ($Tyr^{10}$-$^{125}I$)-VIP (32 μM) mixed with increasing VIP concentrations was treated with the IgG in the absence (●) and presence (▲) of VIP[22–28]

Because VIP[22–28] bound the autoantibody the strongest in comparison to the other homologs, it was screened for catalytic inhibitory activity by measuring its effect on catalysis by the autoantibody. Hydrolysis of increasing concentrations of VIP in the absence and presence of VIP [22–28] was compared. The plot of the reciprocal rate of VIP hydrolysis versus the reciprocal concentration of VIP (FIG. 13) was linear, indicating conformity with Michaelis-Menten kinetics. $K_m$ and $k_{cat}$ values for the VIP cleavage in the absence of VIP[22–28] were 115±14 nM and 6.5±0.3 min$^1$, respectively. In the presence of 100 μM VIP[22–28], the apparent $K_m$ was increased (159±4 nM) and $k_{cat}$ was unchanged (6.9±0.2 min$^1$), suggesting competitive inhibition of VIP hydrolysis. $K_I$ for VIP[22–28] calculated from these data was 260 μM. VIP(22–28] treated with the IgG did not itself undergo cleavage.

It was assumed that the binding and hydrolysis of VIP is mediated by the same autoantibody present in the IgG because: (i) Scatchard analysis of VIP binding suggested that the IgG contains a single class of VIP binding antibody (6); (ii) specific antibody purified from the IgG by binding to VIP coupled to a solid support was found to hydrolyze (Tyr$^{10}$-$^{125}$I)VIP at the same peptide bond (Gln$^{16}$-Met$^{17}$) as the starting IgG; and (iii) the subsequence VIP[22–28] not only inhibited the binding of full length VIP by the IgG, but also its hydrolysis. The reactivity of VIP[22–28] with the catalytic autoantibody appears to be sequence-specific because: (i) inhibition of (Tyr$^{10}$-$^{125}$I)VIP binding and hydrolysis by the VIP[22–28] was competitive in nature; (ii) the inhibition was observed despite presence of an excess (>300-fold, by weight) of an unrelated protein (BSA); and (iii) 400 μM VIP[1–7], a non-binding fragment, did not inhibit VIP hydrolysis. This assumption was confirmed by affinity chromatography of the IgG on VIP-Sepharose.

VIP[22–28] does not contain the scissile peptide bond (Gln$^{16}$-Met$^{17}$) but it binds the catalytic autoantibody and inhibits antibody-catalyzed VIP hydrolysis. Thus, amino acid residues distant from the site of the chemical reaction are believed to be important in substrate recognition and binding by the antibody. Antibody binding pockets appeared to be relatively large, capable of contacting as many as 16 amino acids of antigen (20). VIP[22–28] bound the catalytic autoantibody with significant energy (4.6 kcal/mol), but this energy is only 41% that of VIP[15–28]. These data suggest that VIP[15–28] is the epitope recognized by the catalytic antibody, and VIP[22–28] is a 'subepitope' that contributes some, but not all antibody binding interactions. This conclusion is consistent with previous findings that small fragments of protein antigens usually show low affinity binding to antibodies raised against the parent proteins (21). The exact contribution of residues 15–21 of VIP in binding to the catalytic autoantibody is uncertain. Linear VIP fragments consisting of residues 15–21, 11–17 and 13–20 did not interact significantly with the catalytic autoantibody in the binding assays, but the residues at the scissile bond (Gln$^{16}$-Met$^{17}$) must contact the catalytic group(s) in the antibody active site in some manner. One or more residues in VIP (15–21) may be integral to a conformational determinant recognized by the autoantibody. On the other hand, these residues may contribute relatively nonspecifically to increase the binding energy of VIP[22–28), since N-terminal extension of small peptides with irrelevant amino acids or octanoyl groups is known to increase their antibody binding affinity (22).

Conventional peptidases hydrolyze a broad range of proteins with specificities dictated primarily by the type of amino acids at or in the immediate vicinity of the scissile bond (23). In the case of relatively specific peptidases like renin (24), 3 or 4 amino acid residues located on each side of the cleavage site can influence enzyme binding, Even in these cases, it is believed that binding of substrate subsequences devoid of the scissile bond has not been shown. In contrast, the catalytic autoantibody exhibits significant binding of residues 22–28 of VIP, located 4 amino acids distant from the scissile bond. The recognition of a distant peptide sequence may be interpreted to reflect an extraordinary substrate specificity of this catalytic antibody, compared to conventional peptidases. There is evidence in the case of enzymes that binding energy from interactions at residues other than those at the scissile bond is utilized to increase the catalytic rate (25). It is believed that binding at residues 22–28 of VIP facilitates catalysis by the antibody.

In another preferred embodiment of the invention, the inhibitor is a naturally occurring compound which binds to and thereby inhibits the catalytic activity of anti-VIP catalytic autoantibody. As stated earlier, it had been discovered that little or no VIP hydrolytic activity was present in the IgG fraction of serum isolated from individuals having the anti-VIP catalytic autoantibody when it was tested directly after purification on immobilized protein G (6). However, VIP-hydrolytic activity was observed after subjecting the IgG to ultrafiltration. It has now been discovered that removal of a tightly bound naturally occurring inhibitor imparts VIP-hydrolytic activity to the autoantibody. Thus, in accordance with the invention, the naturally occurring inhibitor of anti-VIP catalytic autoantibody is prepared by collecting serum from an animal having the autoantibody, separating the gamma globulin fraction from the serum by methods known in the art, subjecting the gamma globulin fraction to ultrafiltration in order to separate lower molecular weight molecules from the gamma globulin fraction and then screening the lower molecular weight molecules in the ultrafiltrate for binding and inhibitory activity. Fractions of the ultrafiltrate testing positive for inhibitory activity are further purified and the chemical structure of the inhibitors are identified by methods known in the art.

It has been observed that airway disorders, in particular asthma and bronchitis, are associated with VIP autoantibodies, some of which possess catalytic activity (9). The disease causing potential of catalytic antibodies directed against self-antigens like VIP is greater than that of antibodies that merely bind self-antigens. Thus, high affinity peptide homologs and naturally occurring inhibitors like those just described can be used to treat airway disorders, in particular asthma.

The invention will be more fully described and understood with reference to the following examples which are given by way of illustration.

EXAMPLE 1

Preparation of Mono ($^{125}$I-TYR$^{10}$)-VIP

Purified porcine VIP (Bachem) was labeled with $^{125}$iodine by the chloramine-T method (26). The resulting mono ($^{125}$I-Tyr$^{10}$)-VIP was purified on a Seppak C18 cartridge followed by reverse phase HPLC with a gradient of acetonitrile in trifluoroacetic acid. Two major peaks of radioactivity were obtained (FIG. 1), corresponding to compounds that reacted with rabbit anti-VIP antiserum in radioimmunoassay. In order to obtain sufficient peptide for sequencing, VIP was iodinated with $^{125}$I diluted with $^{127}$I to reduce the specific activity, and purification performed as before. Analysis of the peak with retention time 25.3 min on an Applied Biosystems sequanator with on-line phenylthiohydantoin amino acid detection showed radioactivity mainly in cycle 10, with HPLC characteristics similar to those of monoiodotyrosine (purchased from Calbiochem), indicating that this material was mono($^{125}$I-Ty$^{10}$)-VIP. The second peak of radioactivity (retention time 27.8 min) was identified as di($^{125}$I-Tyr$^{10}$,Tyr$^{22}$)-VIP by similar methods. The di($^{125}$I Tyr$^{10}$,Tyr$^{22}$)-VIP and mono($^{125}$I-Tyr$^{10}$)-VIP performed nearly equivalently in a radioimmunoassay test. Since native VIP, VIP oxidized with chloramine-T without Na$^{125}$I(CT-VIP) and mono ($^{125}$I,Tyr$^{10}$)-VIP were well separated, it was concluded that the $^{125}$I-VIP was free of unlabeled peptide.

EXAMPLE 2
Demonstration of VIP Autoantibodies in Human Subjects

The antibodies were measured in plasma samples from asthma patients and healthy subjects, subdivided into high exercise (Hx) and low exercise (Lx) subgroups (8). Asthma was diagnosed on the basis of patient history and typical clinical indicators. The healthy Hx subjects had a history of habitual muscular exercise, and the healthy Lx subjects did not. Human blood samples were collected in a mixture of peptide hydrolase inhibitors (aprotinin, phenylmethylsulfonyl fluoride, pepstatin, ethylene diamine tetracetic acid) (9). The immunoglobulin G (IgG) fraction from blood was prepared by sequential chromatography (7,9) on DEAE-cellulose (Whatman) and protein G-Sepharose (Pharmacia). The IgG (4 mg/ml) was ultrafiltered on a YM-10 membrane having an average cut off molecular weight of 10,000 Daltons using an Amicon Model 8 MC apparatus to 27 mg/ml, diluted back to 0.8 mg/ml and then subjected to a second cycle of ultrafiltration. The final concentration of IgG prepared in this manner was about 20 mg/ml. Electrophoretic analysis and staining of nitrocellulose blots with anti-human IgG conjugated to peroxidase did not reveal presence of non-immunoglobulin material in this preparation. The presence of VIP-antibodies was established by measuring saturable binding of mono($^{125}$I -Tyr$^{10}$)-VIP (binding inhibited by excess unlabelled VIP) in plasma samples or purified IgG. The monoiodinated form of VIP was used because it is more likely to reproduce the interactions of native VIP with the antibodies. Bound and free VIP were separated by precipitation with polyethylene glycol or specific sheep antibodies against human IgG (9). Plasma samples from some asthma patients and healthy subjects were observed to exhibit saturable $^{125}$I-VIP binding activity (up to 67.5% of total $^{125}$I -VIP). The VIP-antibodies were found in 18% of asthma patients (N=74), 30% of healthy Hx subjects (N=51), 2% of healthy Lx subjects (N=44). The mean $^{125}$I-VIP binding values (%B/T with SEM in parentheses) in the antibody positive asthma and Hx subjects were 23.4 (5.3) and 20.4 (3.2). The lone antibody positive subject in the Lx group showed a % B/T value of 12.1%.

EXAMPLE 3
Hydrolysis of VIP by Anti-VIP Autoantibodies

To compare antibody mediated hydrolysis and spontaneous hydrolysis of the peptide VIP, mono($^{125}$I-Tyr$^{10}$)-VIP was incubated with (i) immune and (ii) nonimmune IgG for increasing lengths of time. IgG from a nonimmune human subject and a VIP antibody positive subject was prepared by chromatography on DEAE cellulose followed by ultrafiltration as described in Example 2. The IgG or assay diluent (final volume of 200 µl in 50 mM Tris-HCl, 100 mM glycine, 0.025% Tween-20 and 0.1% bovine serum albumin, pH 8.0) was incubated with mono ($^{125}$I,Tyr$^{10}$)-VIP (approximately 30 p) for increasing lengths of time at 38° C. Bovine serum albumin and Tween-20 were included in these incubations to prevent adsorptive loss of the mono ($^{125}$I, Tyr$^{10}$)-VIP on glass and plastic surfaces. Precipitation with trichloroacetic acid (TCA) (27) was used as the initial criterion of mono($^{125}$I,Tyr$^{10}$)-VIP degradation (6). Accordingly, 1 ml of TCA (final concentration 10% v/v) was added to the reaction mixtures which were then centrifuged at 3000 xg. The supernatants were aspirated and the radioactivity was measured in the pellets (Beckman model 5500 spectrometer). At this TCA concentration, greater than 90% of intact mono ($^{125}$I,Tyr$^{10}$)-VIP was precipitated (i.e., found to appear in the TCA-insoluble pellet). Values for VIP hydrolysis were computed from the radioactivity observed as counts per minute (CPM) in the TCA-precipitable fractions as:

$$(CpM_{assay\ buffer} - CPM_{antibody}) \times 100 / CPM_{assay\ buffer}.$$

Compared to 8% hydrolysis of the mono ($^{125}$I,Tyr$^{10}$)-VIP incubated with nonimmune IgG, 73% of the peptide was hydrolyzed by treatment with immune IgG.

The ability of the IgG to hydrolyze mono($^{125}$I,Tyr$^{10}$)-VIP was not lost by precipitation with 50% saturated ammonium sulfate or ultrafiltration on a 100 kDa membrane filter. Treatment of the IgG with rabbit anti-human IgG or treatment at 100° C. (10 min) prior to incubation with mono ($^{125}$I,Tyr$^{10}$)-VIP destroyed the hydrolytic activity of the IgG as indicated by a reduction in the amount of radioactivity in the peak with RT of 10 min.

Figure 2:
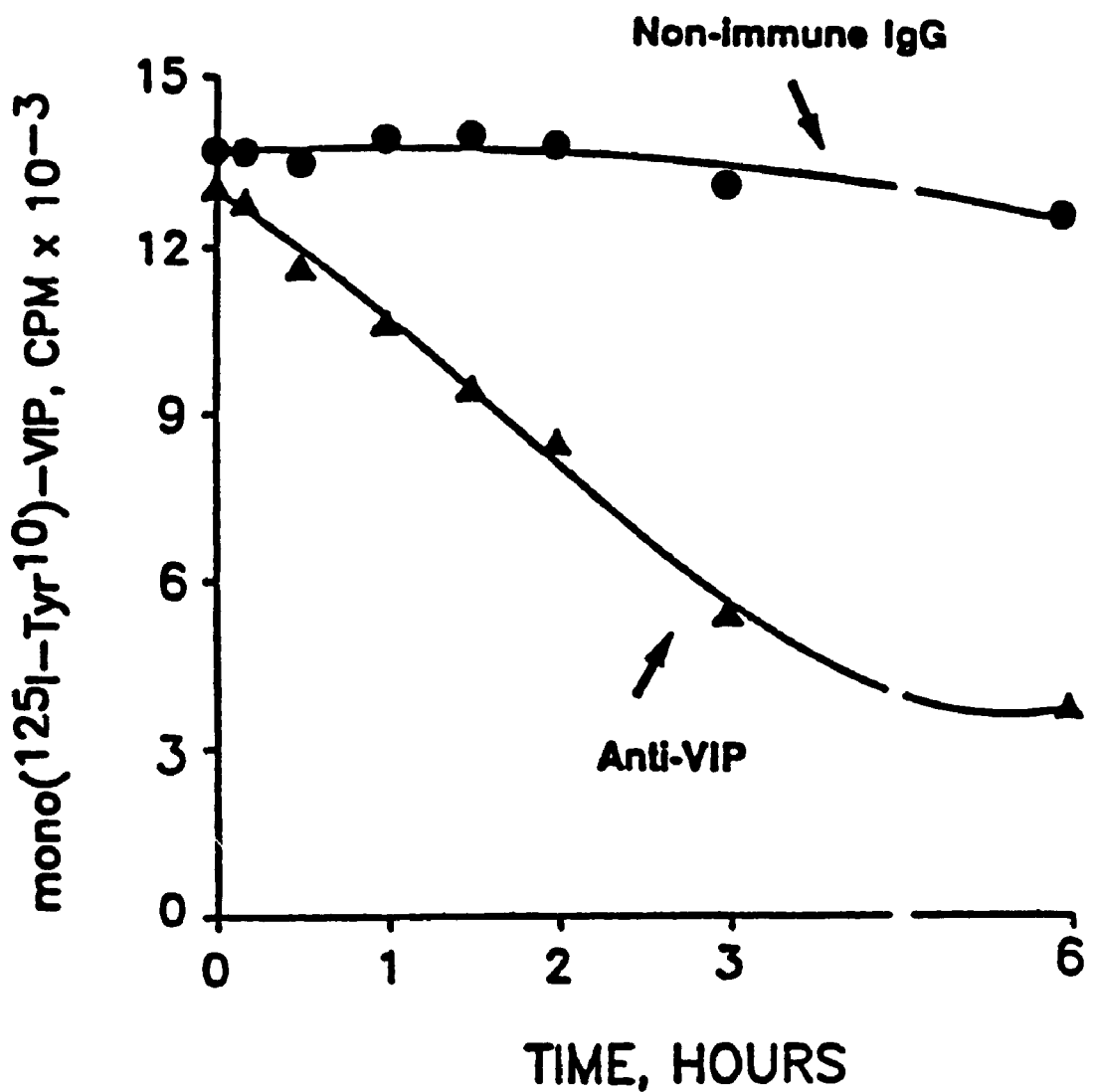
FIG. 2 shows reduced precipitation of mono($^{125}I$, $Tyr^{10}$)-VIP treated with 42.5 ug of the anti-VIP antibody fraction (▲) as compared to an equivalent concentration of a non-immune antibody fraction (●)

Treatment of mono ($^{125}$I,Tyr$^{10}$)-VIP with immune IgG for increasing time periods progressively reduced the amount of radioactivity precipitated by 10% TCA (starting radioactivity in each tube was 15,040 CPM), as shown in FIG. 2. After incubation with immune IgG for 6 h, 73% of the starting mono ($^{125}$I,Tyr$^{10}$)-VIP was no longer precipitated by TCA, compared to only 8% of the mono ($^{125}$I,Tyr$^{10}$)-VIP incubated with nonimmune IgG. The degradation of mono ($^{125}$I-Tyr$^{10}$)-VIP was pH dependent, with an optimum pH of 8.0–8.5.

Figure 3:
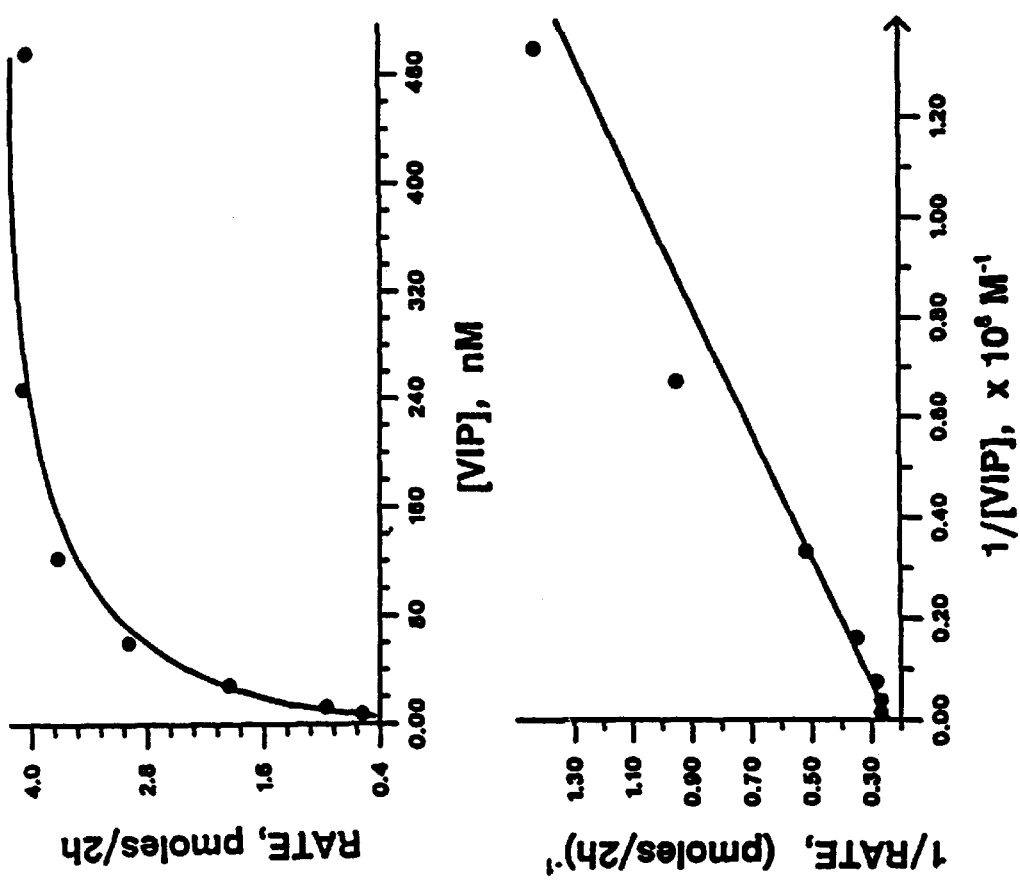
FIGS. 3 shows plots of kinetic data of mono-($^{125}I$, $Tyr^{10}$)-VIP hydrolysis by IgG obtained by incubating IgG with increasing concentrations of unlabeled VIP mixed with a fixed concentration of mono-($^{125}I$, $Tyr^{10}$)-VIP.
Figure 4:
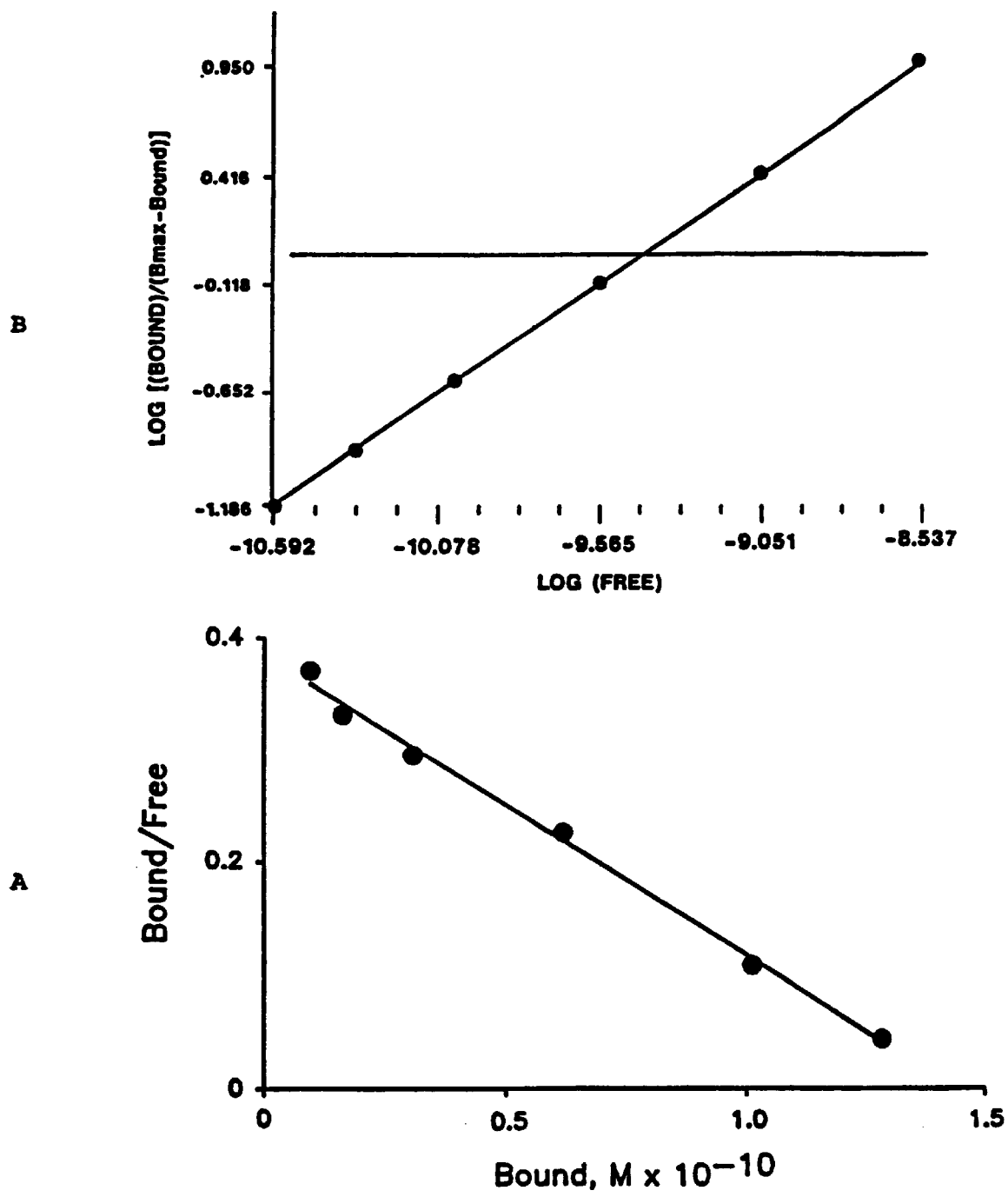
FIG. 4 shows a Scatchard plot (panel A) and Hill plot (panel B) of VIP binding by IgG.

Kinetic data were obtained by incubating IgG with increasing concentrations of unlabeled VIP mixed with a fixed concentration of mono ($^{125}$I, Tyr$^{10}$)-VIP as trace for 2 h at 38° C. The hydrolysis was saturable with increasing VIP concentrations and a plot of 1/velocity vs. 1/substrate concentration was linear, as shown in FIG. 3, indicating that the reaction conformed to Michaelis-Menten kinetics (data fitted to Michaelis-Menten equation using ENZFITTER (Elsevier)). A $K_m$ for the reaction of 37.9 nM, determined from the slope of the linear plot in FIG. 1, indicated relatively stable antibody-VIP binding. A Scatchard plot of VIP binding by the antibody, under conditions that did not lead to VIP hydrolysis, was linear, as shown in FIG. 4A. The slope for the Hill plot, shown in FIG. 4B, was close to unity (1.02). These data indicated a single antibody class with $K_d$ 0.4 nM and concentration 73.4 fmol/mg IgG (assuming antibody bivalency). The $k_{cat}$ and $k_{cat}/K_m$ values for the hydrolysis, computed on the basis of the kinetics of hydrolysis and the antibody concentrations obtained from the binding data, were 0.26 sec$^{-1}$ and 6.9×10$^{M-1}$sec$^{-1}$. These values indicated that the anti-VIP acts catalytically to hydrolyse VIP. A turnover of 0.26 sec$^{-1}$ (i.e., about 16 molecules of VIP are hydrolyzed by one molecule of antibody per minute) was calculated. This calculation was based on the total number of antibodies which were capable of binding to VIP. However, in reality, not all antibodies capable of binding to VIP are necessarily capable of catalytic hydrolysis of VIP. Therefore, the actual turnover number is probably greater than that calculated.

Figure 5:
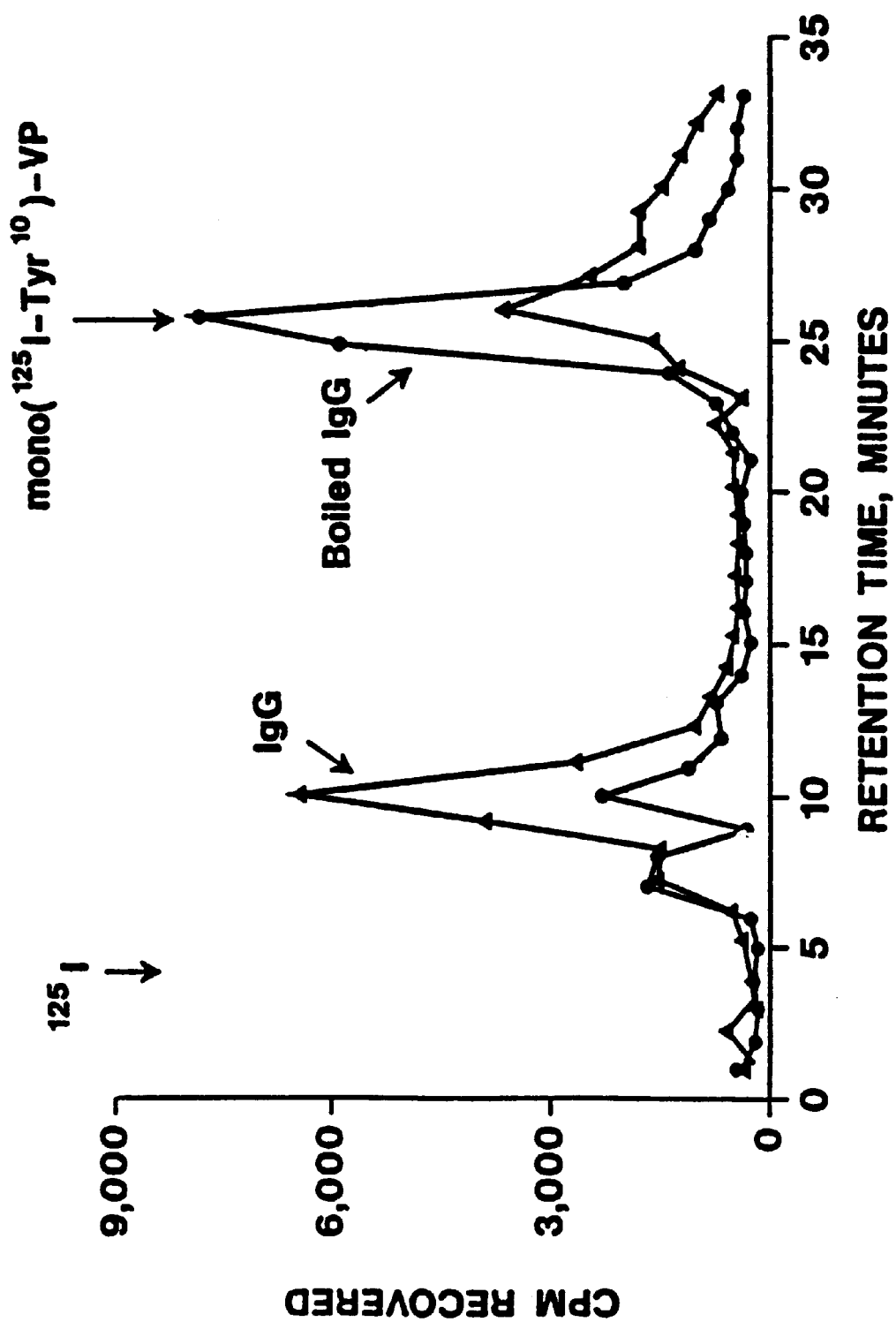
FIG. 5 shows the reverse phase HPLC of mono ($^{125}I$, $Tyr^{10}$)-VIP treated with intact IgG or IgG boiled for ten minutes.
Figure 6:
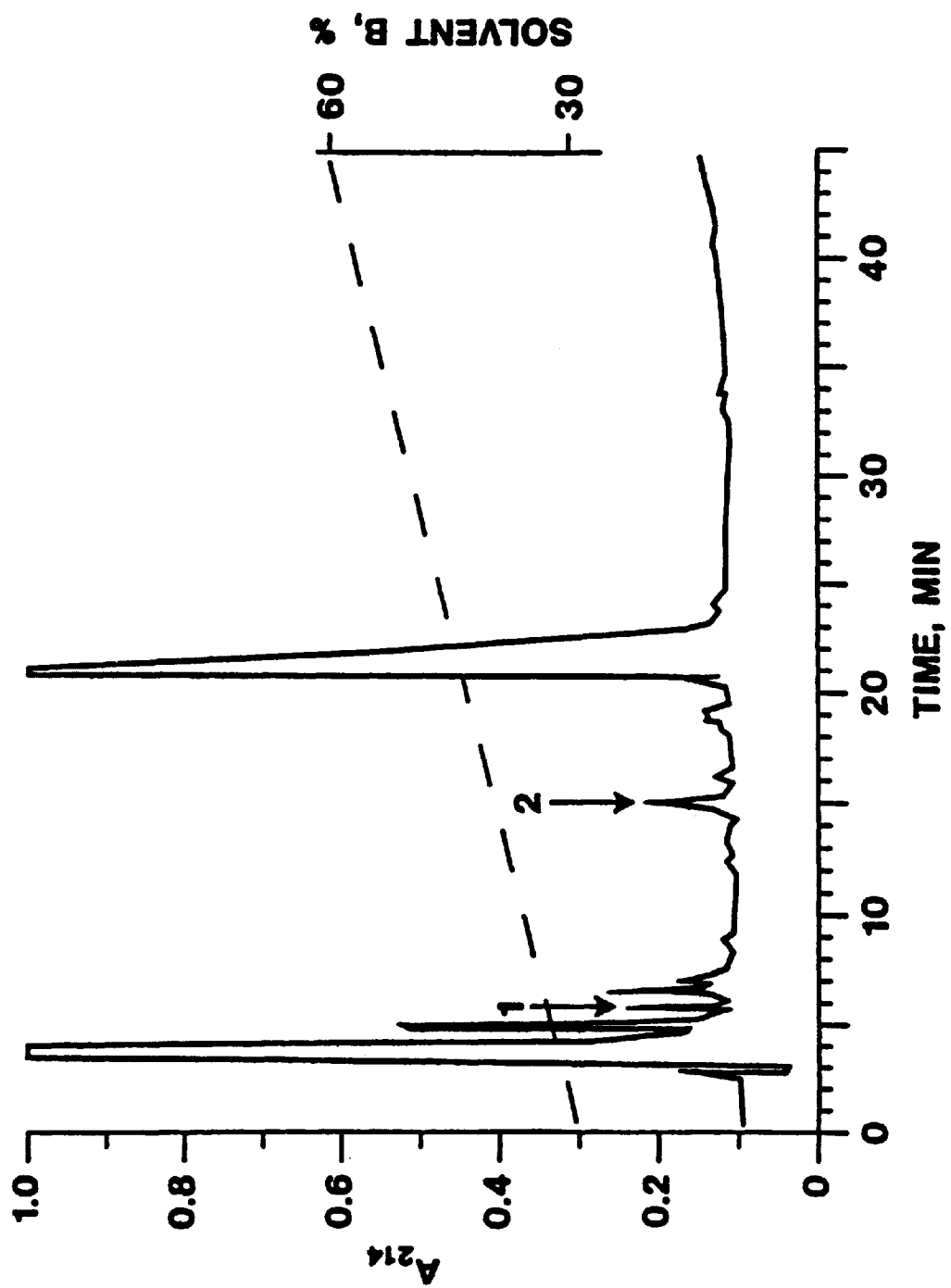
FIGS. 6, 7 and 8 show reverse phase HPLC purification of VIP fragments produced by treatment with the anti-VIP antibody fraction.
Figure 7:
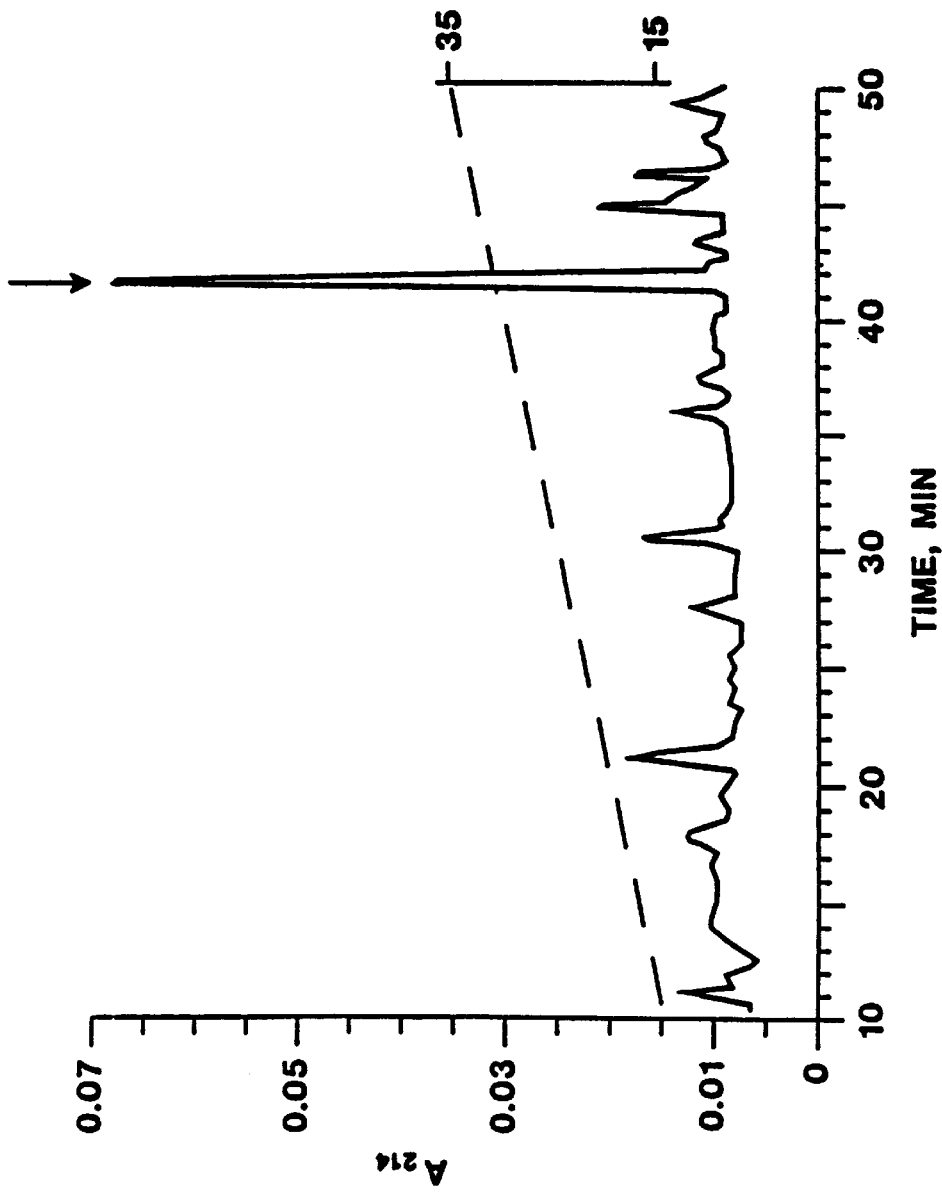
Figure 8:
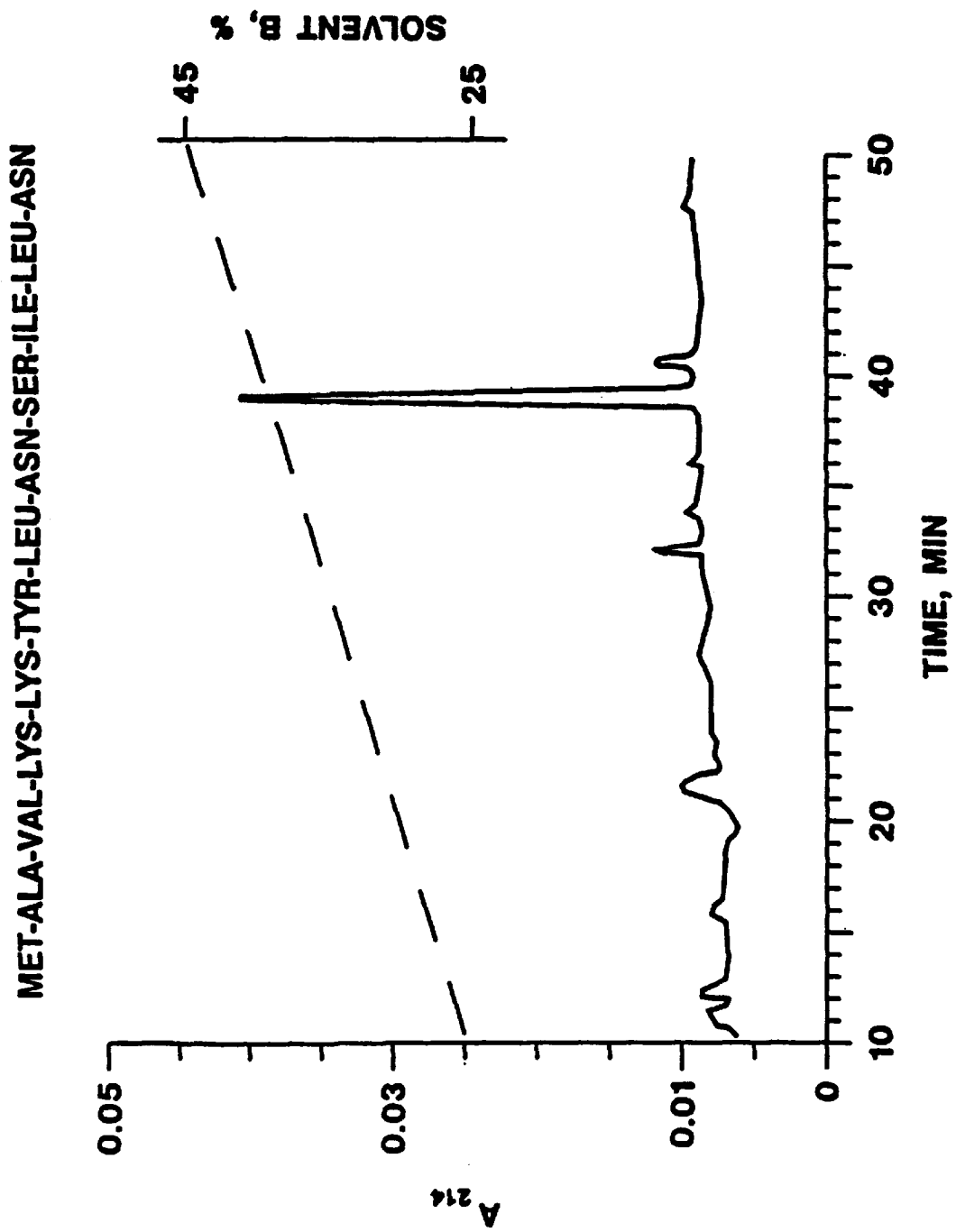
Figure 9:
FIG. 9 shows a partial positive ion fast atom bombardment-mass spectrum (m/z 1200–1500) of the VIP fragment (2) purified in FIG. 8.

EXAMPLE 4
Identification of Peptide Fragments Resulting from Hydrolysis of VIP Catalyzed by Anti-VIP Autoantibodies Reverse phase HPLC of mono ($^{125}$I-Tyr$^{10}$)-VIP treated with the immune IgG revealed a reduction in the amount of intact mono ($^{125}$I,Tyr$^{10}$)-VIP (retention time (RT): 25 min.) and the appearance of an early eluting peak of radioactivity (RT: 10.0 min) that was well separated from intact mono ($^{125}$I-Tyr$^{10}$)-VIP and free $^{125}$I (RT: 65–7.0 min) (FIG. 5). Heat treatment of the IgG prior to incubation with mono (Tyr$^{10}$, $_{125}$I)-VIP resulted in a reduction in the amount of radioactivity in the peak with RT 10 min. When mono ($^{125}$I,Tyr$^{10}$)-VIP was incubated in buffer instead of the IgG, the bulk of the radioactivity was recovered in the form of intact peptide and only 13.9% in the peak with RT of 10 min. In order to purify the fragments of VIP, unlabelled VIP (50 μg) was treated with 525 μg immune IgG or nonimmune IgG as before, except that bovine serum albumin was omitted from the reaction mixture. The reaction mixtures were extracted on Extract Clean C18 cartridges (Alltech), and then subjected to reverse phase HPLC on a Novapak-C18 column (Waters), eluting with a gradient of acetonitrile in trifluoroacetic acid. The absorbance of the eluate was monitored at 214 nM. Two A$_{214}$ nm absorbing peaks (labeled 1 and 2 in FIG. 6), noted after treatment of the VIP with immune IgG, were absent in peptide preparations treated with nonimmune IgG or assay buffer. These peaks were purified by a second round of reverse phase HPLC using shallower gradients for elution (FIGS. 7 and 8). The peptide fractions purified by reverse phase HPLC were dried, and sequenced using an Applied Biosystems pulsed liquid phase sequenator (model 477A) with on-line phenylthiohydantoin-amino acid detection. This procedure demonstrated unequivocally that the major A$_{214}$ absorbing peaks identified as 1 and 2 in FIGS. 7 and 8, respectively, were VIP[1–16] and VIP[17–28]. Fast atom bombardment (f.a.b.)-mass spectrometry of peptide 2 in FIG. 8 and intact VIP(1–28) was performed in the positive ion mode on a VG Analytical ZAB-2SE spectrometer (acceleration potential:8 kV)(M-Scan) using peptides dissolved in 5% acetic acid and thioglycerol/glycerol or m-nitrobenzyl alcohol matrices. Mass calibration was performed with cesium iodide or cesium iodide/glycerol. The F.a.b.-mass spectrometric analysis (FIG. 9) suggested that the molecular mass of peptide 2 was 1393 daltons corresponding to the molecular ion of VIP[17–28]. It is believed that the additional peak observed with mass of 1415 daltons probably represented the sodium adduct of VIP[17–28]. Analysis of VIP[1–28] resulted in a signal at 3325 daltons that corresponded well to the molecular ion of the peptide. Amino acid sequencing of the purified fragments produced by hydrolysis of VIP by the autoantibody showed that the scissile bond is Gln$^{16}$-Met$^{17}$ (6).

EXAMPLE 5
Induction of Catalytic Activity in Anti-VIP-Autoantibody by Removal of Inhibitors A. Ultrafiltration IgG was prepared by chromatography on (i) protein G conjugated to Sepharose or (ii) DEAE-cellulose. The IgG (4 mg/ml) was ultrafiltered on a YM-10 membrane having an average cut off molecular weight of 10,000 Daltons using an Amicon Model 8 MC apparatus to 27 mg/ml, diluted back to 0.8 mg/ml and then subjected to a second cycle of ultrafiltration. The final concentration of IgG prepared in this manner was 20 mg/ml. IgG purified as above but without ultrafiltration and IgG purified and with ultrafiltration as above were each incubated with mono($^{125}$I-Tyr$^{10}$)-VIP in radioimmunoassay buffer at 4° C. for two hours in the presence of increasing unlabeled VIP concentrations and the TCA soluble radioactivity was determined as described in Example 4.

Figure 10:
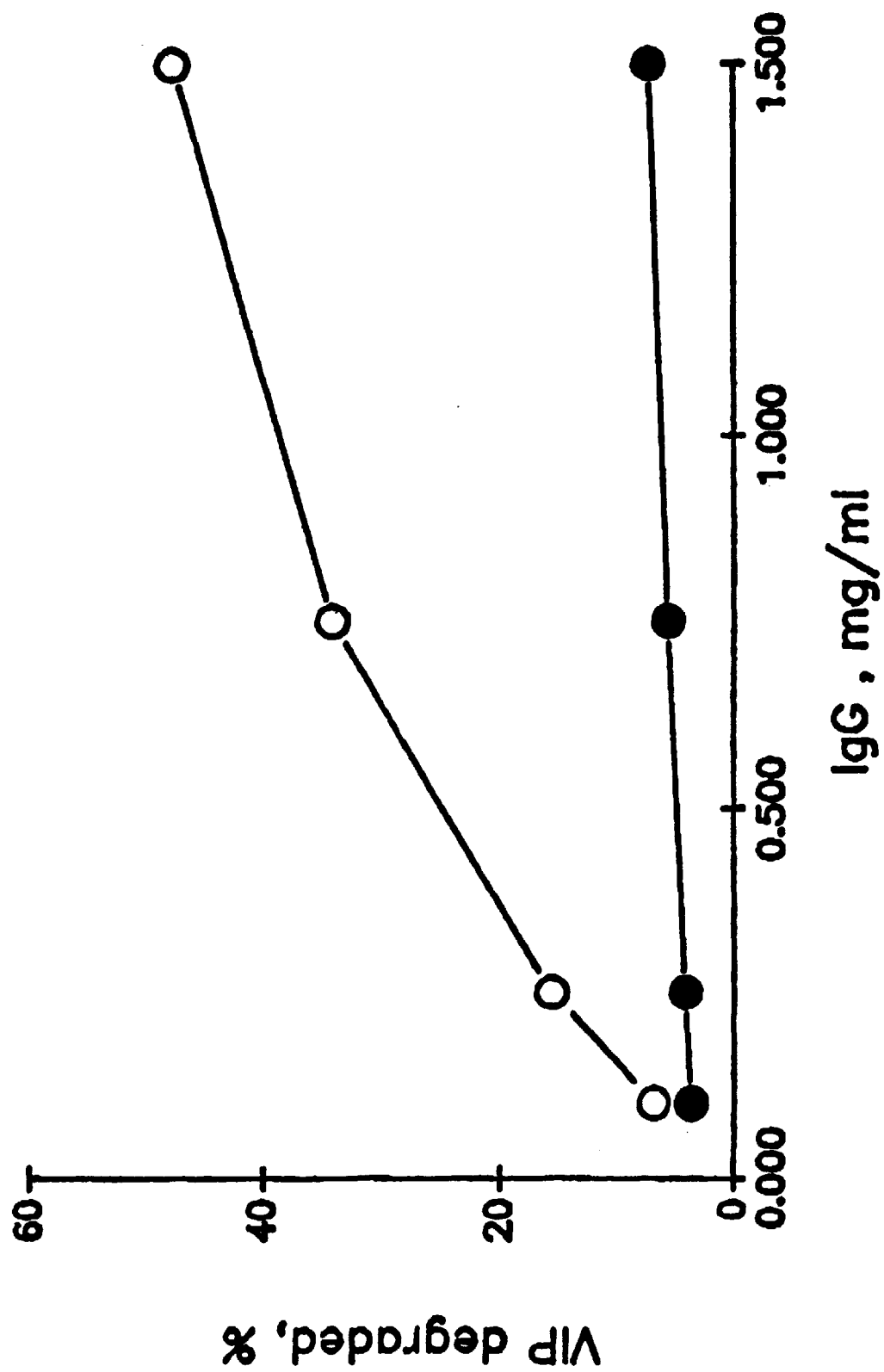
FIG. 10 is a plot of % VIP degraded versus concentration of IgG which (i) received no ultrafiltration (●) and (ii) received ultrafiltration (○)

FIG. 10 indicates that treatment of mono($^{125}$I, Tyr$^{10}$)-VIP with IgG that had not been subjected to ultrafiltration resulted in a dose-dependent, but low-level degradation of the peptide, judged by the increase in TCA-soluble radioactivity over the value obtained with assay buffer. IgG subjected to ultrafiltration degraded VIP better than IgG which had not been ultrafiltered.

B. Dialysis

IgG (2 mg/ml), prepared by chromatography as described in A above, was dialyzed using a dialysis membrane with a cut-off of 12,000–15,000 Daltons for four days against 1000 volumes of buffer (50 mM Tris-HCl, 100 mM glycine, pH 8.0, containing 0.025% Tween-20), with daily buffer changes (a total of three changes). As with ultrafiltration, IgG subjected to dialysis degraded VIP better than IgG which had not been subjected to dialysis.

C. Washing After Immobilization On Protein-G

IgG (1 mg in 0.5 ml of buffer (50 mM Tris-HCl, 100 mM glycine, pH 8.0, containing 0.025% Tween-20)), prepared by chromatography as described in A above, was applied to a Protein G-Sepharose column (settled volume, 3.3 ml) in order to immobilize the IgG on the Protein G. The immobilized IgG was then washed with 135 ml of neutral pH buffer (50 mM Tris-HCl, pH 7.3) followed by elution with a low pH buffer (100 mM glycine-HCl, pH 2.7). The acidic eluent was then neutralized immediately and the IgG isolated. As with ultrafiltration, IgG subjected to neutral buffer washes degraded VIP better than IgG which had not been subjected to such treatment.

D. Affinity Chromatoegraphy on VIP-Sepharose

IgG fractions containing VIP hydrolytic autoantibodies exhibit relatively tight binding of VIP. This property was used to purify specific catalytic VIP hydrolytic autoantibodies on a VIP-Sepharose column. IgG was purified from the plasma of a human subject by ammonium sulfate precipitation and DEAE-cellulose chromatography (9). The IgG was free of detectable nonimmunoglobulin materials (6). To prepare the affinity chromatography matrix, synthetic VIP (1–28) (10 mg) mixed with about 20 pg (Tyr$^{10}$-$^{125}$I)-VIP was covalently coupled to 5 g CNBr-Sepharose (5 g; Pharmacia) in 0.1 M NaHCO$_3$, pH 7, in 0.5 M NaCl for two hours at 4° C., and unreacted groups on the gel were quenched with 0.2 M glycine in coupling buffer (28). The coupling efficiency was greater than 90%, based on incorporation of (Tyr$^{10}$-$^{125}$I)-VIP. About 90 mg IgG was shaken with 4.5 ml of VIP-Sepharose gel at 4° C. and 0.5 M Tris-HCL, pH 8.0 for 2 h. The mixture was poured into a column, the gel washed with buffer until the effluent A$_{280}$ (sensitivity 0.05 AUFS) returned to baseline, and bound IgG was eluted with 0.1 M glycine-HCl, pH 2.7 and neutralized immediately with 1 M Tris-HCl, pH 9.0. Antibody concentrations were estimated by scans (A$_{562}$) of silver-stained, non-reducing SDS-gels, using authentic IgG as standard (Gilford Response II spectrophotometer). Increasing authentic IgG concentrations (2–20 ng per lane) showed a linear increase in A$_{562}$ values. As with ultrafiltration, IgG subjected to affinity chromatography degraded VIP better than IgG which had not been subjected to affinity chromatography.

EXAMPLE 6
Preparation of VIP Homologs

Synthetic peptide homologs of VIP were prepared for screening for inhibitory activity. Ten synthetic peptides (FIG. 11), corresponding to 7-mer, 16-mer and 14-mer linear subsequences of VIP, were prepared by solid phase synthesis using methods known in the art (29) at the University of Florida Protein Structure Care Facility, Gainsville, and their identity was confirmed by amino acid composition analysis. Reverse phase HPLC on a C-18 column revealed a single $A_{214}$ absorbing peptide in each of the preparations. Peptide content of each of these preparations was >80%. Full length VIP[1–28] was from Bachem.

EXAMPLE 7

Screening of VIP Homologs for Inhibition of VIP-Catalytic Autoantibody

A. Screening for Binding Activity

The ten synthetic peptides were screened for the ability to bind $(Tyr^{10}-^{125}I)$-VIP. The peptides were incubated with the autoantibody IgG fraction and $(Tyr^{10}-^{125}I)$-VIP in a buffer which was non-permissive for VIP hydrolysis, i.e., in 7.5 mM sodium phosphate, pH 7.4, 0.64% sodium chloride, 0.5% bovine serum albumin, 25 mM EDTA, 0.005% bacitracin, 0.005% protamine sulfate, 0.073% sodium azide and 0.025% Tween-20.

IgG purified from the plasma of a human subject was the source of the autoantibody. Plasma, prepared by centrifugation of blood, was precipitated with 50% saturated ammonium sulfate, the precipitate reconstituted in 50 mM Tris-HCl, pH 8.0, dialyzed against this buffer and IgG purified by chromatography on DEAE cellulose (9). The IgG showed a single silver-stained protein band on SDS-polyacrylamide gels with molecular mass 150 kD, that reacted with peroxidase conjugated anti-human IgG in immunoblots (6).

Scatchard analysis of IgG-VIP binding suggested that the IgG contained a single type of VIP binding antibody (6). This conclusion was supported by the observation that a VIP specific antibody purified from this IgG preparation was capable of mono-$(Tyr^{10}-^{125}I)$-VIP hydrolysis.

Affinity purification of the catalytic antibody was by chromatography on VIP coupled covalently to CNBr-Sepharose as described in Example 5. The bound antibodies were eluted with acid (pH 2.7) and brought to neutral pH. Reducing SDS-polyacrylamide gel melectrophoresis of this material revealed two silver stained protein bands with mass 58 kD and 25 kD, stainable with anti-human H-chain (IgG) and anti-human Lchain antibodies, respectively, in immunoblots. Analytical isoelectric focusing and silver staining on Phastgels (pH gradient 3 to 10; Pharmacia) revealed a series of closely spaced bands with pI 6.8–8.4, indicating a restricted antibody population. The affinity fractionated autoantibodies hydrolyzed $(Tyr^{10}-^{125}I)$ VIP ($K_m$:0.12 $\mu$M) at the same peptide bond ($Gln^{16}$-$Met^{17}$ as the starting IgG (1), judged by coelution of the reaction product, $(Tyr^{10}-^{125}I)$VIP (1–16), with authentic $(Tyr^{10}-^{125}I)$VIP(1–16) in reverse phase HPLC analyses.

Binding assays were conducted at 4° C. for 20 h (6). The amount of $(Tyr^{10}-^{125}I)$-VIP precipitated by 10% trichloroacetic acid after incubation in buffer and immune IgG was similar (85.6% and 82.6% of the total amount of radioactivity available, respectively), indicating that $(Tyr^{10}-^{125}I)$-VIP was not cleaved by the IgG under these conditions.

The N-terminal fragment VIP[1–16] at a concentration >$10^7$-fold larger than $(Tyr^{10}-^{125}I)$-VIP failed to displace binding of the radioactive ligand by the autoantibody. In contrast, the C-terminal fragment VIP[15–28] inhibited the binding with potency ($K_I$ 1.25 nM) close to that of the full length peptide, VIP[1–28] ($K_D$ 0.3 nM) (FIG. 12; data, means of duplicates corrected for nonspecific binding observed in the presence of 1 $\mu$M VIP, were compiled from these experiments). Saturable binding observed without competitor peptides ranged from 4053 to 6012 CPM, and nonspecific binding was approximately 600 CPM. The apparent $K_D$ or $K_I$ for VIP, VIP[15–28] and VIP[22–28] were obtained using the EBDA and LIGAND programs (Elsevier). It was assumed that (i) the binding reaction had reached equilibrium, and (ii) $K_D$ for $(Tyr^{10}-^{125}I)$-VIP and unlabeled VIP was the same. Free energy of binding, $\Delta F$, was computed as: F=−RTlnK$_A$, where R is the gas constant at normal temperature and pressure, T is the reaction temperature (277° K.) and $K_A$ is the apparent association constant ($1/K_D$ or $1/K_I$). $K_I$ was computed from the equation $K_m^{app}=K_m(1+[I]/K_I)$ where [I] is the inhibitor concentration.

Of the remaining seven shorter peptides tested initially at concentrations of 500 $\mu$M each, only VIP[22–28] and VIP[18–24] inhibited the autoantibody from binding $(Tyr^{10}-^{125}I)$-VIP. The $K_I$ for VIP[22–28] was 242.1 $\mu$M. VIP[22–28] showed approximately 8-fold greater binding potency than VIP[18–24], suggesting that the reactivity of the latter peptide may be due to the shared sequence, VIP[22–24]. Approximate binding energy values for these peptides were, in kcal/mole, VIP[1–28], 12.1; VIP[15–28], 11.3; and, VIP[22–28], 4.6. The binding energy of residues 22–28 was substantial, although only 38% of that for the full length peptide.

B. Screening for Inhibition of Anti-VIP Catalytic Activity by VIP [22–28]

Because VIP[22–28] exhibited significant binding to the autoantibody, its ability to inhibit the catalytic activity of the autoantibody was determined. The hydrolyses of increasing concentrations of VIP in the absence and presence of VIP [22–28] were compared. $(Tyr^{10}-^{125}I)$-VIP, 32 pM, was mixed with increasing VIP concentrations and was treated with the autoantibody, 50 $\mu$g IgG, in the absence and presence of VIP[22–28] (100 $\mu$M) for three hours at 38° C. The plot of the reciprocal rate of VIP hydrolysis versus the reciprocal concentration of VIP was linear, indicating conformity with Michaelis-Menten kinetics (FIG. 13; values were means of duplicates, fitted to the Michaelis-Menten equation by means of the ENZFITTER (Elsevier) program). The $K_m$ and $k_{cat}$ values for the VIP cleavage in the absence of VIP[22–28) were 115±14 nM and 6.5±0.3min$^{-1}$, respectively. In the presence of 100 $\mu$M VIP[22–28], the apparent $K_m$ was increased (158.6±4.4 nM) and $k_{cat}$ was unchanged (6.9±0.2 min$^{-1}$), suggesting competitive inhibition of VIP hydrolysis. $K_I$ for VIP[22–28], computed from the equation $K_m^{app}=K_m(1+[I]/K_I)$ where [I] is the inhibitor concentration, was 260 $\mu$M. Inhibition was observed in the presence of an excess (>300-fold, by weight) of bovine serum albumin. In addition, 400 $\mu$M VIP(1–7), a non-binding fragment, did not inhibit VIP hydrolysis.

6 $\mu$g VIP[22–28] was treated with assay diluent or IgG using incubation conditions identical to those employed to hydrolyze VIP[1–28], and the reaction mixture was extracted on a C-18 Seppak cartridge and analyzed by reverse phase HPLC (6), using a gradient of acetonitrile (8–64% in 45 min) in 0.1% trifluoroacetic acid. The amounts of VIP[22–28] (retention time=39.1 min) recovered after incubation in diluent and IgG were not significantly different, judged by the areas of the $A_{214}$ absorbing peptide peaks, indicating that VIP[22–28] did not undergo cleavage.

VIP[22–28] does not contain the scissile peptide bond ($Gln^{16}$-$Met^7$) but, as shown by the data above, it bound the autoantibody and inhibited autoantibody catalyzed VIP hydrolysis.

EXAMPLE 8

Purification and Identification of Naturally Occurring Inhibitor(s) of catalytic Antibodies Directed Against VIP The result of Example 5 prompted the conclusion that each of the four induction methods, i.e., ultrafiltration, dialysis, washing after immobilization on Protein-G and affinity chromatography on VIP-Sepharose, removed a tightly bound inhibitor, thereby imparting VIP hydrolytic activity to the autoantibody. In order to isolate, purify and identify the inhibitor, the ultrafiltrate, dialysate, neutral buffer washings from the Protein-G column or buffer washings from the affinity chromatography containing the inhibitor is concentrated to 3 ml and extracted on a Seppak C-18 Cartridge. Retained material is eluted with acetonitrile in 0.1% trifluoroacetic acid, dried in vacuo and subjected to reverse phase HPLC on a C-8 or C-18 column.

Aliquots of column fractions are screened for binding activity as described in Example 7A and for inhibitory activity as described in Example 7B by mixing with $(Tyr^{10}\text{-}^{125}I)$-VIP and catalytic IgG, incubation for 3 h at 38° C. and precipitation with 10% trichloroacetic acid. In control tubes, hydrolysis of the VIP is measured in assay diluent instead of the column fractions. Fractions showing inhibitory activity are pooled and subjected to further separation procedures in order to yield the pure inhibitor. These separation procedures include ion exchange chromatography and chromatofocusing (30). The pure inhibitor is subjected to amino acid analysis and peptide sequencing on an Applied Biosystems sequenator. Once the identity of the inhibitor is known, it is synthesized in large quantity using standard solid phase peptide synthesis methods (29). The synthetic inhibitor is then used to specifically inhibit the catalytic autoantibody, resulting in the alleviation of pathogenesis of the autoimmune disorder (asthma) caused by the catalytic autoantibody (anti-VIP-autoantibody).

EXAMPLE 9

Characterization and Catalytic Activity of IgG Purified by Affinity Chromatography (Fractionation) on VIP-Sepharose A. VIP Hydrolysis $(Tyr^{10}\text{-}^{125}I)$-VIP (about 30 pM) mixed with increasing VIP concentrations was treated with the IgG or antibodies purified by affinity chromatography on VIP-Sepharose as in Example 5D for 3 h at 38° C. in 200 µl 0.05 M Tris-HCl, 0.1 M glycine, pH 8, containing 0.025% Tween-20 and 0.1% BSA. The IgG and antibodies tested hydrolysis assays were previously dialyzed against 500 volumes of buffer for 4 days, with daily buffer changes. Hydrolysis of VIP was computed by measuring the radioactivity rendered soluble in TCA, corrected for the radioactivity observed after incubation in assay diluent (6). Catalysis by the antibody was determined in the absence and presence of VIP[22–28]. Data were fitted to the Michaelis-Menten equation by means of the ENZFITTER program (Elsevier). Reverse phase HPLC of antibody treated reaction mixtures was on a C18 column (6).

B. $(Tyr^{10}\text{-}^{125}I)$ VIP Binding

IgG prepared by DEAE-cellulose chromatography was assayed for saturable $(Tyr^{10}\text{-}^{125}I)$-VIP binding (9), in the absence and presence of increasing concentrations of unlabeled VIP. Apparent $K_D$ for VIP was determined using EBDA and LIGAND programs (Elsevier) assuming (i) the binding had reached equilibrium, and (ii) the $K_D$ of $(Tyr^{10}\text{-}^{125}I)$-VIP and unlabeled VIP were identical.

C. Sodium Dodecylsulfate—Polyacrylamide Gel Electrophoresis (SDS-PAGE) and Isoelectric Focusing (IEF)

Electrophoresis of antibody preparations treated with 20 mM M 2-mercaptoethanol and 2.5% SDS (100° C., 5 min) was on Phast SDS-gradient gels (8–25%) (Pharmacia). The gel was stained with silver (31). For immunostaining, proteins were transferred to nitrocellulose (BA85, Schleicher and Schuell) by diffusion blotting (30 min), the membrane was treated with blocking buffer (0.02 M Tris-HCl, pH 7.4, 0.5 M NaCl, 3% BSA, 0.05% Tween-20), then with rabbit antihuman H-chain (IgG) (1:1000) or anti-human L-chain (1:2,500) (Accurate) for 60 min, washed with buffer, treated with peroxidase conjugated goat anti-rabbit IgG (1:1000; Accurate), washed again and finally incubated with 0.5 mg diaminobenzidine/ml (Sigma) and 0.03% hydrogen peroxide for 10–30 min. IEF was on Phast IEF gels using a pH gradient of 3–10 constructed with Pharmalytes.

Figure 14:
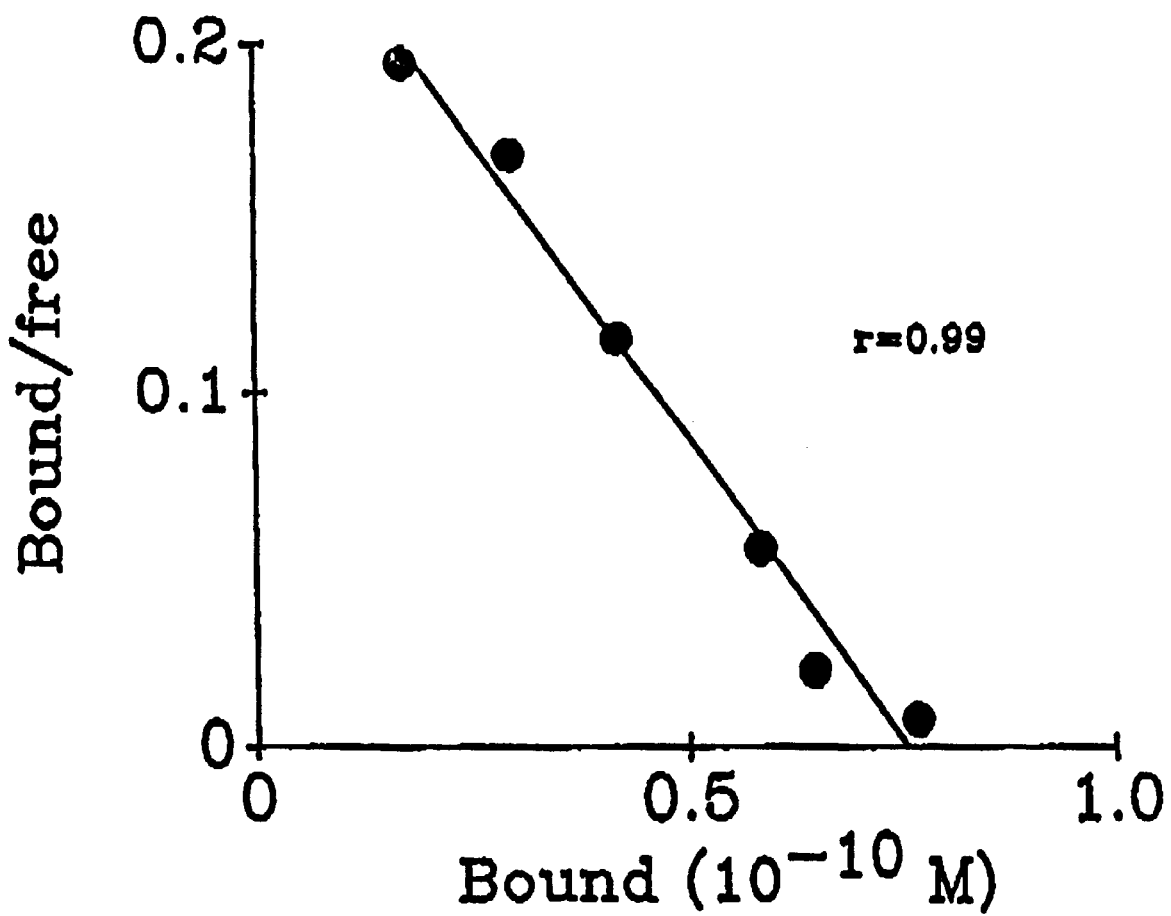
FIG. 14 is a Scatchard plot of VIP binding by the IgG.
Figure 15:
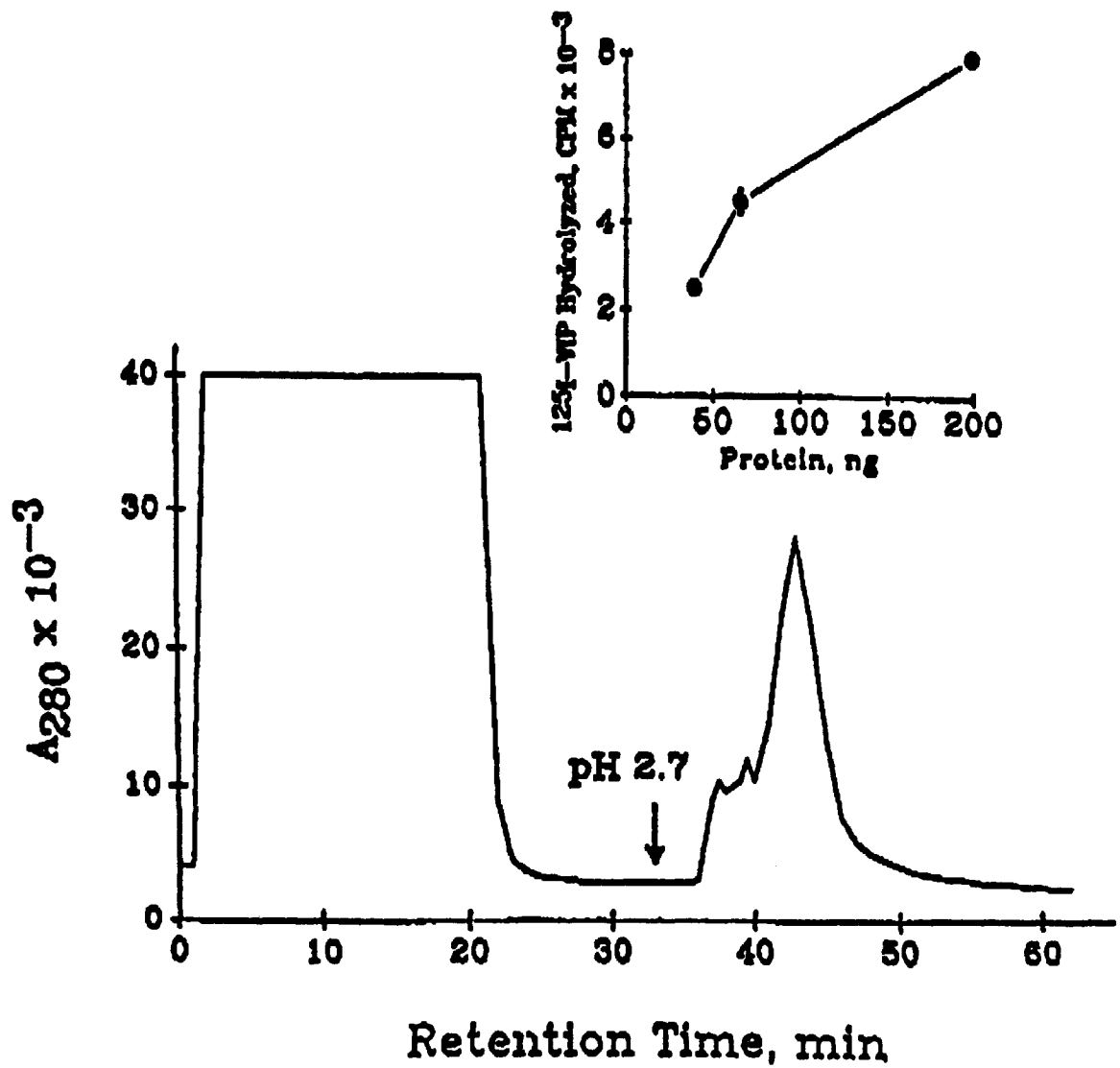
FIG. 15 shows an affinity chromatograph of human IgG on a VIP-Sepherose column, with the arrow indicating the shift to a low pH buffer and the inset shows hydrolysis of ($Tyr^{10}$-$^{125}I$) VIP as a function of concentration of acid eluted antibody concentration.
Figure 16:
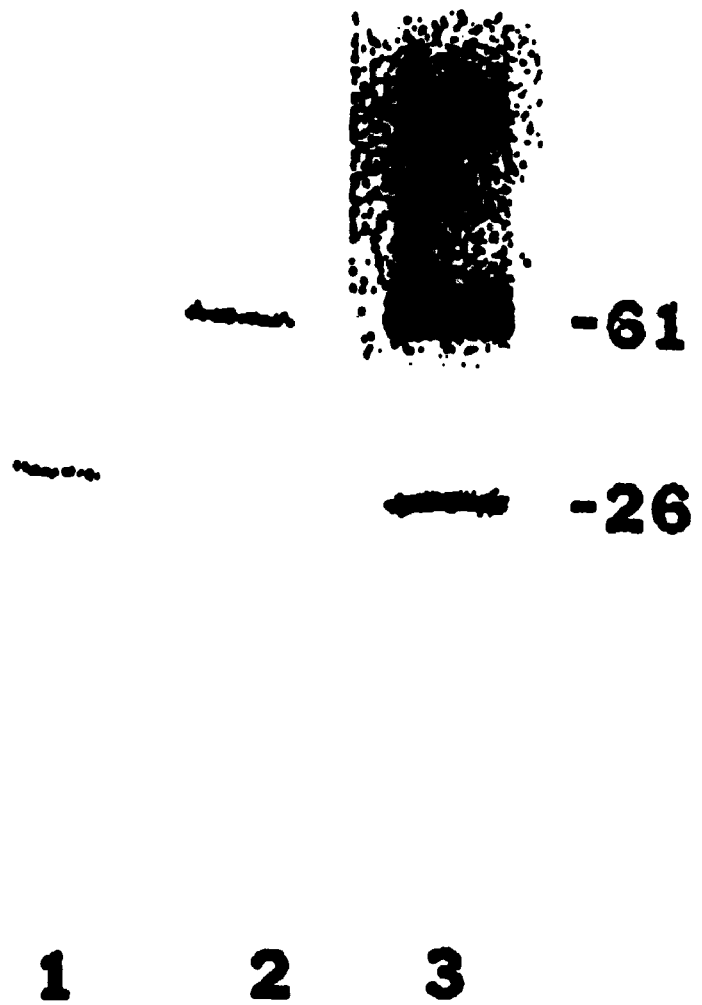
FIG. 16 shows reducing SDS-polyacrylamide gel electrophoresis of affinity-fractionated VIP autoantibodies stained with anti L-chain antibody (lane 1), anti-H-chain antibody (lane 2) and silver (lane 3)

D. Characterization of Anti-VIP Catalytic Autoantibody $(Tyr^{10}\text{-}^{125}I)$-VIP to VIP binding was measured using IgG that did not exhibit measurable VIP hydrolytic activity (i.e., IgG which had not been subjected to ultrafiltration, dialysis, Protein-G chromatography or affinity chromatography on VIP-Sepharose) judged by the amount of radioactivity precipitated in 10% TCA after incubation in assay diluent or immune IgG (87.9% and 91.0%). A Scatchard plot of VIP binding by the IgG revealed a single binding component (r=0.99) with $K_d$ 0.3 nM and VIP antibody concentration 184 fmol/mg IgG (FIG. 14; values shown in FIG. 14 are means of three replicates each). Progressively increasing $(Tyr^{10}\text{-}^{125}I)$VIP hydrolysis by increasing concentrations of the affinity-purified antibodies was observed, judged by the amount of radioactivity rendered soluble in TCA (FIG. 15). SDS-PAGE under reducing conditions indicated that the affinity-fractionated material was composed of 61 kD H-chains and 26 kD L-chains, judged by silver staining and reactivity with anti-H and anti-L chain antibodies in immunoblots (FIG. 16). The IEF profile of the affinity-fractionated preparation (pH range 3.0–10.5) revealed a restricted range of antibody species (approximately 12 closely spaced bands focused at pH 6.9–8.4), compared to unfractionated IgG (innumerable bands focused mainly at pH 7.1–9.5).

E. Hydrolytic specificity and Catalysis by VIP Antibodies

Figure 17:
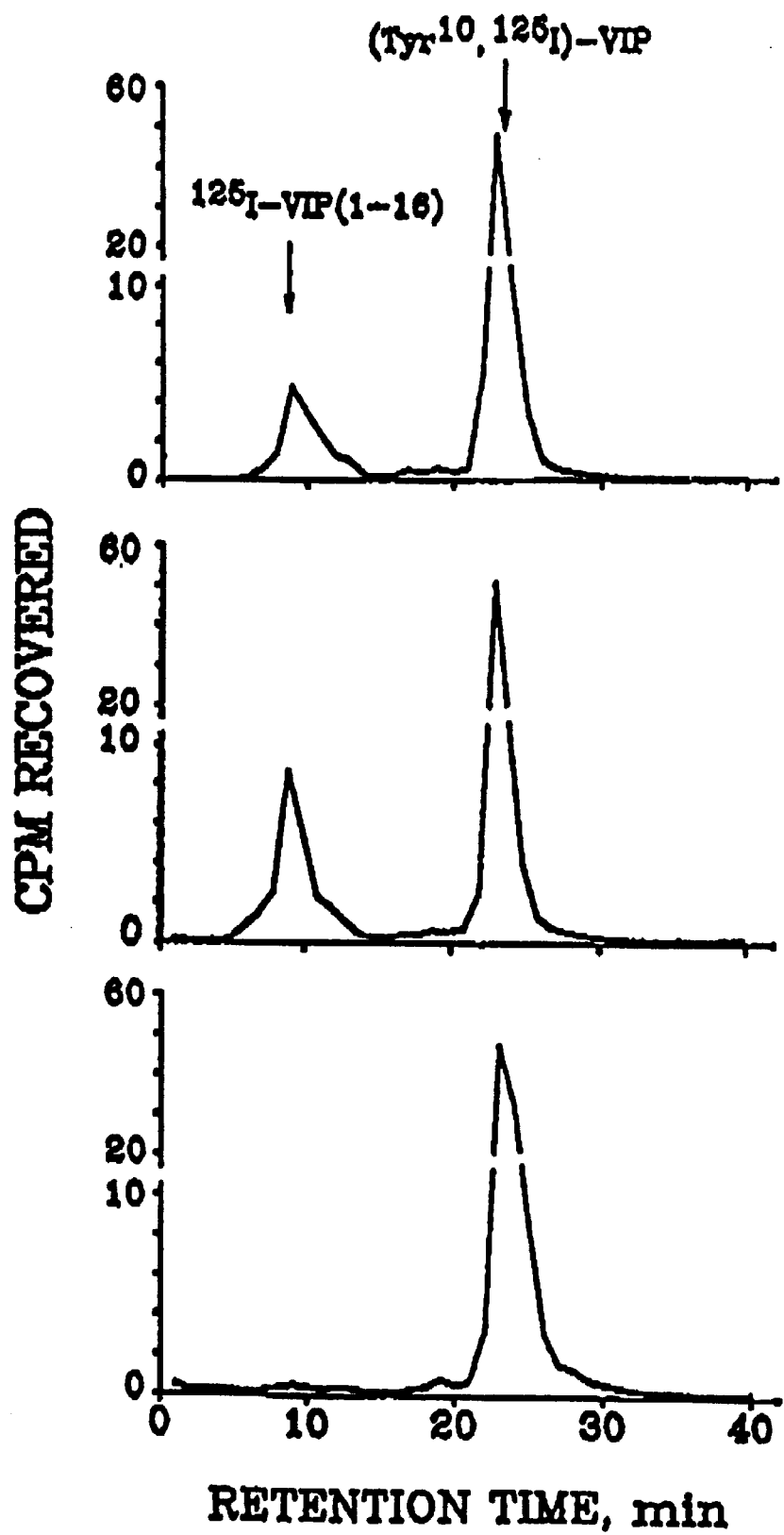
FIG. 17 shows reverse phase HPLC of ($^{125}I$, $Tyr^{10}$)-VIP treated with unfractionated IgG (upper panel), affininty-fractionated VIP antibodies (middle panel), and assay diluent (lower panel), with arrows showing the retention time of synthetic ($^{125}I$)-VIP[1–16] and unhydrolyzed ($^{125}I$, $Tyr^{10}$)-VIP.
Figure 18:
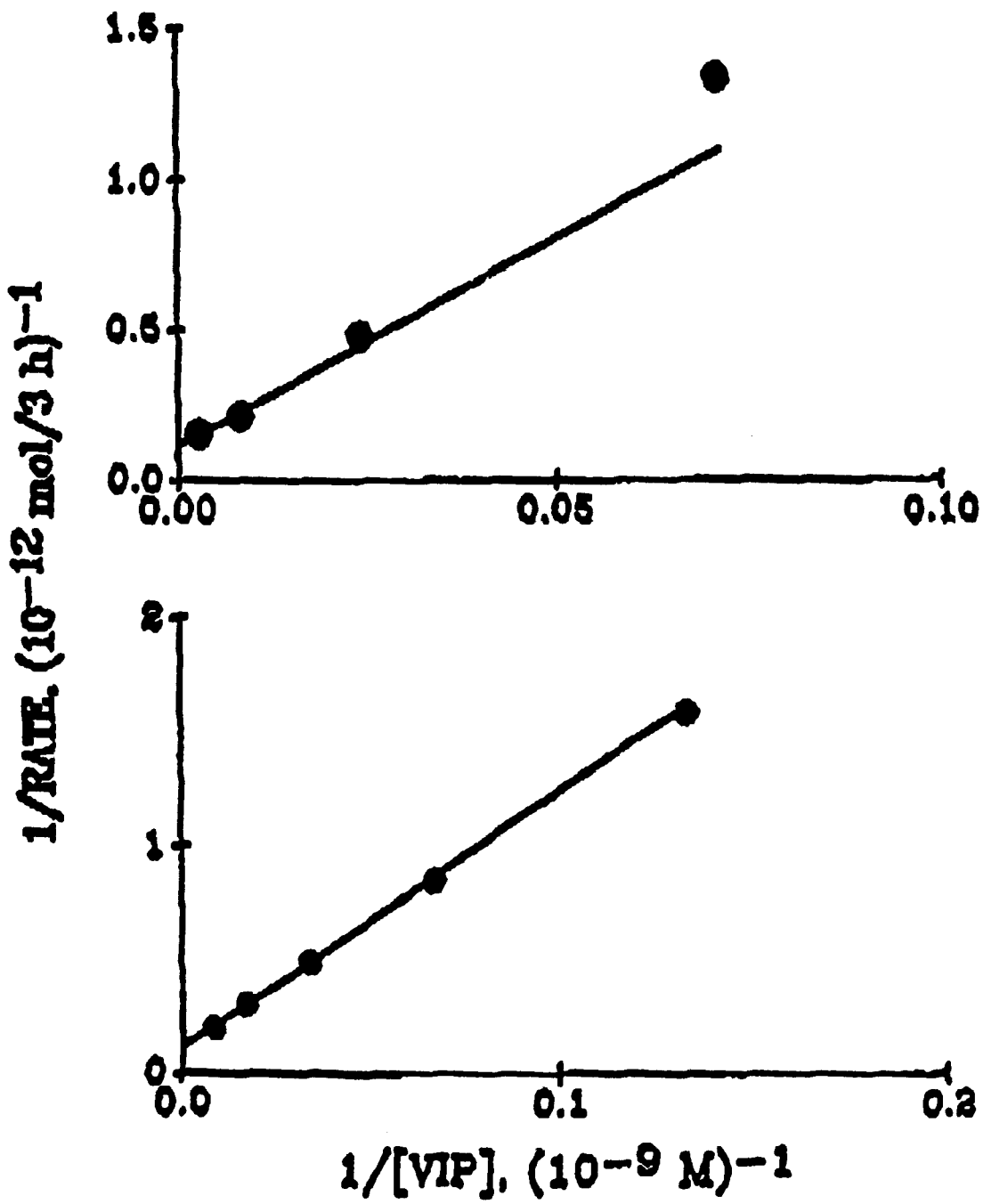
FIG. 18 shows Lineweaver-Burke plots of VIP hydrolysis by affinity-fractionated VIP antibodies (upper panel) and unfractionated IgG (lower panel).

The IgG preparation used here hydrolyzed the $Gln^{16}\text{-}Met^{17}$ bond in VIP (32). Thus, when $(Tyr^{10}\text{-}^{125}I)VIP$ is used as substrate, one radioactive fragment, $(Tyr^{10}\text{-}^{125})VIP(1–16)$, is generated. To compare their hydrolytic specificities, 100 µg of unfractionated IgG and 0.3 µg of affinity-purified antibody were incubated with 210 pg $(Tyr^{10}\text{-}^{125}I)VIP$, and the reaction product characterized by reverse phase HPLC (FIG. 17). Treatment with both types of antibody preparations generated a single radioactive peptide with retention time identical to that of synthetic $^{125}I$-VIP[1–16] (8.2 min). This radioactive peptide was well resolved from unhydrolyzed $(Tyr^{10}\text{-}^{125}I)VIP$ (retention time 21.5 min). These data suggested the peptide generated by the affinity-fractionated antibody and IgG is $(Tyr^{10}\text{-}^{125}I)VIP(1–16]$ and therefore it was concluded that the affinity-purified antibody, like the unfractionated IgG, cleaved the $Gln^{16}\text{-}Met^{17}$ bond. Direct evidence that the antibody is a catalyst was obtained from the saturation kinetics of VIP hydrolysis. The affinity-fractionated antibody preparation was incubated with increasing VIP concentrations and a fixed $(Tyr^{10}\text{-}^{125}I)VIP$ concentration (30 pM), and the radioactivity rendered soluble in TCA was measured. Plots of the reciprocal velocity versus reciprocal VIP concentration for affinity fractionated antibodies (66 ng) and for unfractionated IgG (300 µg) were essentially linear, suggesting conformity with Michaelis-Menten kinetics (FIG. 18). The $K_m$ value for the affinity-fractionated antibody was 110±3 nM, compared to 112±6 nM for unfractionated IgG. The turnover number of the antibody ($k_{cat}$) computed on the basis of the amount of total protein in the assay, was 0.11±0.01 $min^{-1}$. Comparison of the specific activities ($V_{max}$/ng total protein) of the affinity-fractionated antibody preparation and unfractionated IgG indicated a 2076-fold purification factor.

F. Kinetic Study

Study of the saturation kinetics displayed by the affinity-purified preparation provided direct evidence that the VIP-antibody is a catalyst. The antibody appeared to bind VIP relatively tightly ($K_m$ 110 nM), compared to conventional peptidases (33) and antihapten catalytic antibodies which exhibit $K_m$ values usually in the micromolar to millimolar range (34). The apparent high affinity substrate binding property of the VIP antibody is a desirable feature, since it is likely to confer stringent substrate specificity. Given that peptide bond hydrolysis is an energetically demanding chemical reaction, the calculated values of VIP antibody turnover number ($k_{cat}$ 0.11 min$^{-1}$) and kinetic efficiency ($k_{cat}/K_m$ 1.1×10$^6$ M$^{-1}$ min$^{-1}$) are impressive. Although the IEF profile of the affinity-fractionated VIP antibodies revealed a restricted range of antibodies, it remains possible that the preparation may not be a homogeneous one. Thus, the $k_{cat}$ measured for the affinity-fractionated antibody preparation (0.11 min$^{-1}$) is a minimal value. The theoretical $k_{cat}$ value of the VIP antibody present in unfractionated IgG ($V_{max}$/amount of antibody, estimated from as the x-intercept of the Scatchard plot) was 6.5 min$^{-1}$. In comparison, the $k_{cat}$ and $k_{cat}/K_m$ values reported for an amidase antibody raised against a presumed transition state analog are 0.08 min$^{-1}$ and 1.4×10$^2$ M$^{-1}$min$^{-1}$, respectively (35). An antibody capable of Gly-Phe bond cleavage with metal co-factor assistance is purported to be a true catalyst with $k_{cat}$ 0.04 min$^{-1}$, but its saturation kinetics are not described (36).

Other embodiments of the invention will be apparent to those skilled in the art from a consideration of this specification or practice of the invention disclosed herein.

REFERENCES

1. Pauling, L. *Nature* 161:707, 1948.
2. Kohen, F., Kim., J. B., Lindner, H. R., Eshhar, Z., Green, B. Antibody enhanced hydrolysis of steroid esters *FEBS Lett.* 111:427 (1980).
3. Pollack, S. J., Jacobs, J. W., Schultz, P. G. *Science* 234, 1570 (1986); A. Tramontano, A. A. Amman, R. A. Lerner, *J. Am. Chem Soc.* 110, 2282 (1988); K. D. Janda, D. Schloeder, S. J. Benkovic, R. A. Lerner, *Science* 241:1188 (1988); C. N. Durfor, R. J. Bolin, R. J. Sugasawara, R. J. Massey, J. W. Jacobs, P. G. Schultz, *J. Am. Chem. Soc.* 110:8713 (1988).
4. Jackson, D. Y., Jacobs, J. W., Sugasawara, R. Reich, S. H., Bartlett, P. A., Schultz, P. G., *J. Am. Chem. Soc.* 110:4841 (1988); D. Hilvert, S. H. Carpenter, K. D. Nared, N. T. Auditor, *Proc. Natl. Acad. Sci. USA* 85:4953 (1988).
5. Shokat, K, Leumann, C. H., Sugasawara, R., Schultz, P. G., *Angew. Chem. Int. Ed. Engl.* 27:1172 (1988).
6. Paul, S. et al., Catalytic hydrolysis of vasoactive intestinal peptide by human autoantibody. *Science* 244:1158–1161 (1989).
7. Paul, S., H. Erian, P., Said, S. I. Autoantibody to vasoactive intestinal peptide in human circulation. *Biochem. Biophys. Res. Commun.* 130:479–485 (1985).
8. Paul, S., Said, S. I. Human autoantibody to vasoactive intestinal peptide: Increased incidence in muscular exercise. *Life Sciences* 43:1079–1084 (1988).
9. Paul, S., Said, S. I., Thompson, A., Volle, D. J., Agrawal, D. K., Foda, H., De la Rocha, S.: Characterization of autoantibodies to VIP in asthma. *J. Neuroimmunol.* 23:133–142 (1989).
10. Itoh, N., Obata, K.-I., Yanaihara N., Okamoto, H. Human preprovasoactive intestinal polypeptide contains a novel PHI-27-like peptide, PHM-27, *Nature* 304:547–549 (1983).
11. Bloom, S. R., Barnes, A. J., Adrian, T. E., Polak, J. M. Autoimmunity in diabetics induced by hormonal contaminants of insulin. *Lancet* 1:14–17 (1979).
12. Ruff, M. R., Martin, B. M., Ginns, E. I., Farrar, W. L., Pert, C. B. CD4 receptor binding peptides that block HIV infectivity cause human monocyte chemotaxis. *FEBS Lett.* 211:17–22 (1987).
13. Nilsson, A. Structure of the vasoactive intestinal peptide from chicken intestine. The amino acid sequence. *FEBS Lett.* 60:322–326 (1975).
14. Dimaline, R., Thorndyke, M. C. Purification and characterization of VIP from two species of dogfish. *Peptides* 7(Suppl.1):21–26 (1986).
15. Paul, S., Chou, J., Beckham, S., Liu, L.-W, Kubota, E., Dominguez, N., Said, S. I Elevatede-levels of atrial natriuretic peptide and vasoactive intestinal peptide in exercising man. *Clin. Res.* (abstr.) 35:112A (1987).
16. Woie, L., Kaada, B., Opstaad, P. K. Increase in plasma VIP in muscular exercise. *Gen. Pharmacol.* 17:321–326 (1987).
17. Rosselin, G. The receptors for the VIP family peptides (VIP, secretin, GRF, PHI, PHM, GIP, glucagon and oxyntomodulin). Specificites and identity. *Peptides* 7(Suppl. 1):89–100 (1986).
18. Paul, S., Said, S. I. Characterization of receptors for vasoactive intestinal peptide from the lung. *J. Biol. Chem.* 262:158–162(1987).
19. Barret, A. J. and Salvesen, A., eds., Proteinase Inhibitors, Elsevier, London (1986); Meek, L. D. et al., "Inhibition of HIV-1 Protease In Infected T-Lymphocytes By Synthetic Analogues", *Nature* 343:390–392 (1990).
20. Amit, A. G., Mariuzza, R. A., Philips, S. E. V., Poljak, R. J., *Science* 233:747 (1986); S. Sheriff, et al., *Proc. Natl. Acad. Sci.* (*USA*) 84:8075 (1987).
21. van Regenmortel, R. H. V., *Synthetic Peptides as Antigens*, Laboratory Techniques in Biochemistry and Molecular Biology Series, (Eds: R. H. Burdon and P. H. van Knippenberg, 19:1–39 (1988).
22. Benjamini, E., Shimizu, M., Young, J. D., Leung, C. Y., *Biochemistry*, 7:1261 (1968); E. Benjamini, M. Shimizu, J. D. Young, C. Y. Leung, ibid. 7:1253 (1968).
23. Barrett, A. J., *Proteinase Inhibitors*, (Eds. A. J. Barrett and G. Salvesen, Elsevier, 3–22 (1986).
24. Rich, D. H., *Proteinase Inhibitors*, (Eds. A. J. Barrett and G. Salvesen, Elsevier, 179–217 (1986).
25. Paul S. et al., *J. Neuroimmunol.* 23:133 (1989).
26. Paul, S., Wood, K., Said, S. I. Purification of [$^{125}$I]-Vasoactive intestinal peptide by reverse-phase HPLC. *Peptides* 5:1085–1087 (1984).
27. Turner, J. T., Bylund, D. B. Characterization of the VIP receptor in rat submandibular gland: Radioligand binding assay in membrane preparations *J. Pharmacol Exp. Therap.* 242:873–881 (1987).
28. *Affinity Chromatography. Principles and Methods*, Pharmacia, Uppsala, Sweden, 12–18 (1986).
29. (Stewart, J. M. and Young, J. D., *Solid Phase Peptide Synthesis*, Pierce Chemical Co., Rockford, Ill. (1984).
30. FPLC™ Ion Exchange and Chromatofocusing, Pharmacia, Uppsala, Sweden, 1–171 (1985).
31. PhastGel Silver Kit Instruction Manual. Pharmacia (Uppsala, Sweden 1987).
32. Baldwin, E. and Schultz, P. G., Generation of a catalytic antibody by site-directed mutagenesis. *Science.* 244:1152 (1989).
33. Dixon, M., Webb, E. C. et al., *Enzymes*, 3d Ed. Longman, (London 1979); Fisher, G. Acyl group transfer-Aspartic proteinases. *Enzyme Mechanisms*, M. I. Page and A. Williams, eds., Royal Society of Chemistry, 230 (London 1987).
34. Janda, K. D. et al., supra ref. 3; Schultz, P. G. Catalytic antibodies. Acc. Chem. Res. 22:287 (1989); Blockburn, G. M., Kang, A. S. et al. Catalytic antibodies. *Biochem. J.* 262:381 (1989).
35. Janda, K. D. et al., supra ref. 3.
36. Iversen, B. L. and Lerner, R. A., *Science* 243:1184 (1989).

We claim:

1. An inhibitor which inhibits an antibody from catalyzing the cleavage or formation of a peptide bond in a substrate, said inhibitor selected from the group consisting of
   (a) a fragment of the substrate, (b) an analog of a fragment of the substrate, and (c) an analog of the substrate, provided that said inhibitor is not the substrate.

2. An inhibitor which inhibits an autoantibody from catalyzing a chemical reaction of a substrate.

3. An inhibitor as recited in claim 1, wherein said substrate is selected from the group consisting of a peptide, a protein, a hormone, a neurotransmitter and a neurohumoral factor.

4. An inhibitor as recited in claim 2, wherein said substrate is a self-antigen of an animal having said autoantibody.

5. An inhibitor as recited in claim 2, wherein said substrate is selected from the group consisting of a peptide, a protein, a hormone, a neurotransmitter and a neurohumoral factor.

6. An inhibitor as recited in claim 5, wherein said substrate is a peptide.

7. An inhibitor as recited in claim 6 wherein said fragment of said substrate is a homologous peptide.

8. An inhibitor which inhibits an antibody from catalyzing the cleavage or formation of a peptide bond in a substrate, said inhibitor having been prepared by a process comprising the steps of:
   (a) synthesizing at least one fragment of the substrate; or
   (b) synthesizing at least one analog of at least one fragment of the substrate; or
   (c) synthesizing at least one analog of said substrate; and
   (d) screening said fragment or analog synthesized in steps (a)–(c) to identify a fragment or analog which inhibits said antibody, provided that said inhibitor is not the substrate.

9. An inhibitor which inhibits an autoantibody from catalyzing a chemical reaction of a substrate, said inhibitor having been prepared by a process comprising the steps of:
   (a) collecting serum from an animal having said autoantibody;
   (b) separating the gamma globulin fraction from said serum;
   (c) separating from said gamma globulin fraction molecules which bind to said gamma globulin; and
   (d) screening said molecules to identify at least one molecule which is capable of inhibiting said autoantibody.

10. A method as recited in claim 9, wherein said substrate is a peptide and said chemical reaction is the cleavage of a bond in said peptide.

11. An inhibitor which inhibits an autoantibody from catalyzing a chemical reaction of a substrate, said inhibitor having been prepared by a process comprising the steps of:
    (a) synthesizing at least one analog or at least one fragment of said substrate; and
    (b) screening said analog or fragment to identify an analog or a fragment which inhibits said autoantibody.

12. An inhibitor as recited in claim 11, wherein said substrate is a peptide and said chemical reaction is cleavage of a bond in said peptide.

13. A pharmaceutical composition for treating autoimmune disease in an animal wherein an autoantibody, which catalyzes a chemical reaction of a substrate in said animal, contributes to or is responsible for the pathophysiology of said autoimmune disease as a result of said reaction being catalyzed, said composition comprising (a) an inhibitor which inhibits said autoantibody from catalyzing a said chemical reaction, and (b) a pharmaceutically suitable carrier.

14. A pharmaceutical composition for treating asthma which comprises an inhibitor of anti-VIP catalytic autoantibody and a suitable pharmaceutical carrier.

* * * * *